US009981392B2

(12) United States Patent
Kim et al.

(10) Patent No.: US 9,981,392 B2
(45) Date of Patent: May 29, 2018

(54) ARM UNIT AND ROBOT HAVING THE SAME

(71) Applicants: Samsung Electronics Co., Ltd., Suwon (KR); Massachusetts Institute of Technology, Cambridge, MA (US)

(72) Inventors: Yong Jae Kim, Seoul (KR); Sang bae Kim, Cambridge, MA (US); Shan bao Cheng, Cambridge, MA (US); Karl Iagnemma, Cambridge, MA (US)

(73) Assignees: Samsung Electronics Co., Ltd., Gyeonggi-do (KR); Massachusetts Institute of Technology, Cambridge, MA (US)

( * ) Notice: Subject to any disclaimer, the term of this patent is extended or adjusted under 35 U.S.C. 154(b) by 316 days.

(21) Appl. No.: 13/898,888

(22) Filed: May 21, 2013

(65) Prior Publication Data

US 2013/0312564 A1  Nov. 28, 2013

(30) Foreign Application Priority Data

May 25, 2012 (KR) .......... 10-2012-0056374
Nov. 20, 2012 (KR) .......... 10-2012-0131721

(51) Int. Cl.
*B25J 18/06* (2006.01)
*A61B 34/30* (2016.01)

(52) U.S. Cl.
CPC .......... *B25J 18/06* (2013.01); *A61B 34/30* (2016.02); *A61B 2034/306* (2016.02); *Y10S 901/21* (2013.01); *Y10T 74/20323* (2015.01)

(58) Field of Classification Search
CPC ... B25J 9/065; B25J 18/06; A61B 2019/2238; Y10T 74/20311; Y10T 74/20317; Y10T 74/20323
USPC .............. 74/490.02, 490.03, 490.04; 901/21
See application file for complete search history.

(56) References Cited

U.S. PATENT DOCUMENTS

| | | | |
|---|---|---|---|
| 4,393,728 A | * | 7/1983 | Larson .................. B05B 15/061 248/160 |
| 4,494,417 A | * | 1/1985 | Larson et al. .................. 74/469 |
| 4,815,911 A | * | 3/1989 | Bengtsson et al. ............... 414/7 |
| 5,456,568 A | * | 10/1995 | Kirby et al. .................. 414/722 |

(Continued)

FOREIGN PATENT DOCUMENTS

| | | |
|---|---|---|
| JP | S56-003193 A | 1/1981 |
| JP | S5924004 U | 2/1984 |

(Continued)

OTHER PUBLICATIONS

European Search Report dated Sep. 18, 2013 in corresponding European Application No. EP 13169235.

(Continued)

*Primary Examiner* — Terence Boes
(74) *Attorney, Agent, or Firm* — Harness, Dickey & Pierce, P.L.C.

(57) ABSTRACT

An arm unit having an improved configuration to simply change stiffness according to varying situations and a robot having the same are provided. The robot includes an arm unit, and a drive unit to drive the arm unit. The arm unit includes a plurality of links to come into rolling contact with one another via at least two regions thereof, and a plurality of wires penetrating the plurality of links to connect the links to one another.

28 Claims, 22 Drawing Sheets

(56) References Cited

U.S. PATENT DOCUMENTS

| | | | |
|---|---|---|---|
| 6,270,453 B1* | 8/2001 | Sakai | A61B 1/0055 600/141 |
| 2004/0195988 A1* | 10/2004 | Buckingham et al. | 318/560 |
| 2005/0090809 A1 | 4/2005 | Cooper et al. | |
| 2006/0094931 A1 | 5/2006 | Danitz et al. | |
| 2006/0178556 A1* | 8/2006 | Hasser | A61B 1/05 600/102 |
| 2006/0199999 A1* | 9/2006 | Ikeda | A61B 1/00149 600/141 |
| 2008/0287963 A1* | 11/2008 | Rogers | A61B 1/00039 606/130 |
| 2009/0012648 A1* | 1/2009 | Buckingham | B25J 9/06 700/260 |
| 2010/0022918 A1 | 1/2010 | Fujie et al. | |
| 2010/0076266 A1* | 3/2010 | Boulais | A61B 1/00059 600/142 |
| 2012/0071720 A1* | 3/2012 | Banik et al. | 600/118 |
| 2012/0253326 A1* | 10/2012 | Kleyman | 606/1 |

FOREIGN PATENT DOCUMENTS

| | | |
|---|---|---|
| JP | H06-170779 A | 6/1994 |
| JP | 2000-193893 A | 7/2000 |
| JP | 2009-136684 A | 6/2009 |
| KR | 10-2011-0036800 | 4/2011 |
| WO | WO 2010/140844 | 12/2010 |

OTHER PUBLICATIONS

Notification of Due Registration Formalities issue by the State Intellectual Property Office of P.R. China dated Aug. 31, 2017 for CN Application No. 201310183103.1.

Japanese Office Action dated Aug. 22, 2017 for JP Patent Application No. 2013-107170.

Japanese Office Action dated Feb. 14, 2017 for Japanese Patent Application No. 2013-107170.

Second Office Action issued by SIPO dated Jan. 19, 2017 for CN Application No. 201310183103.1.

\* cited by examiner

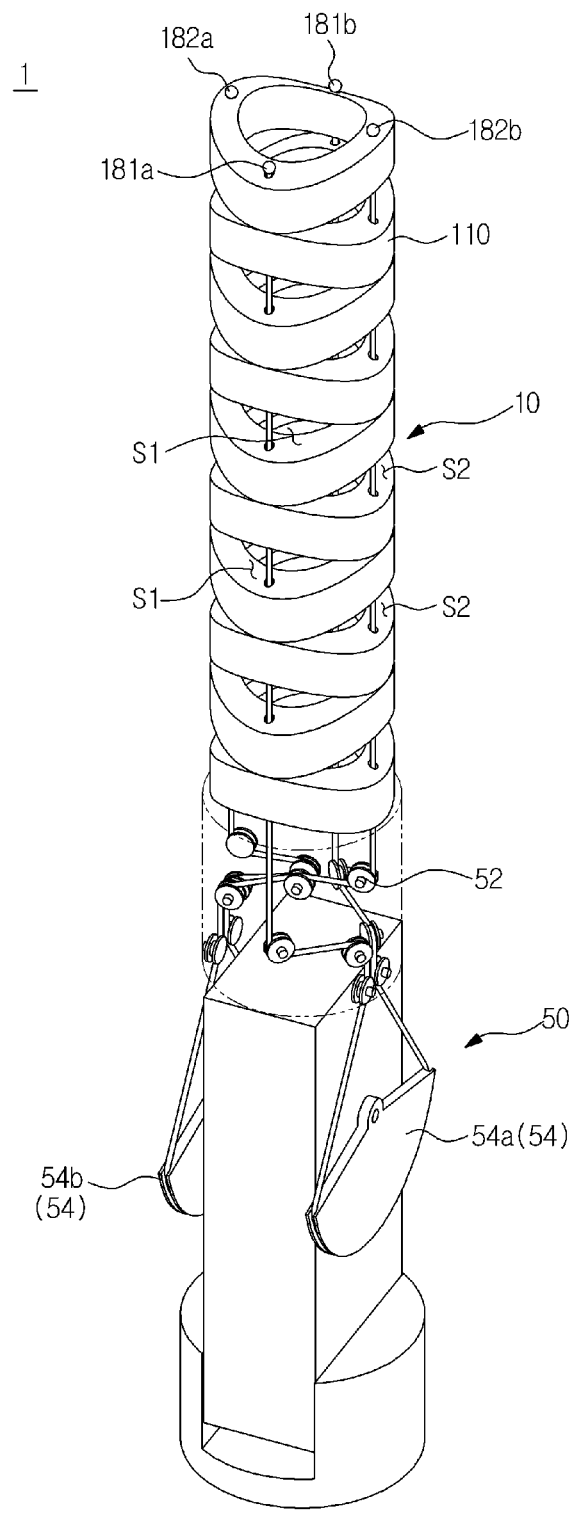
[FIG. 1]

[FIG. 2]
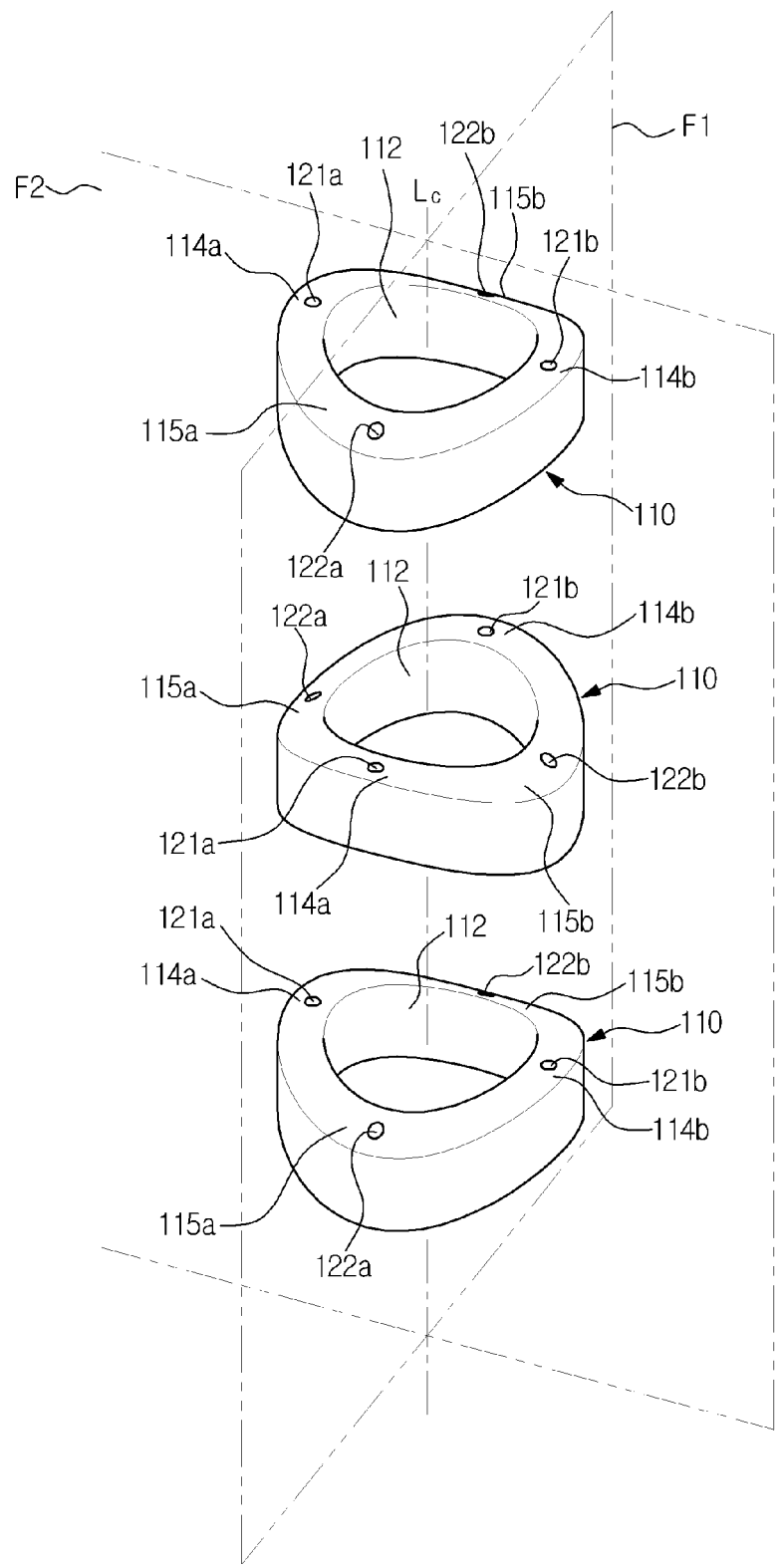

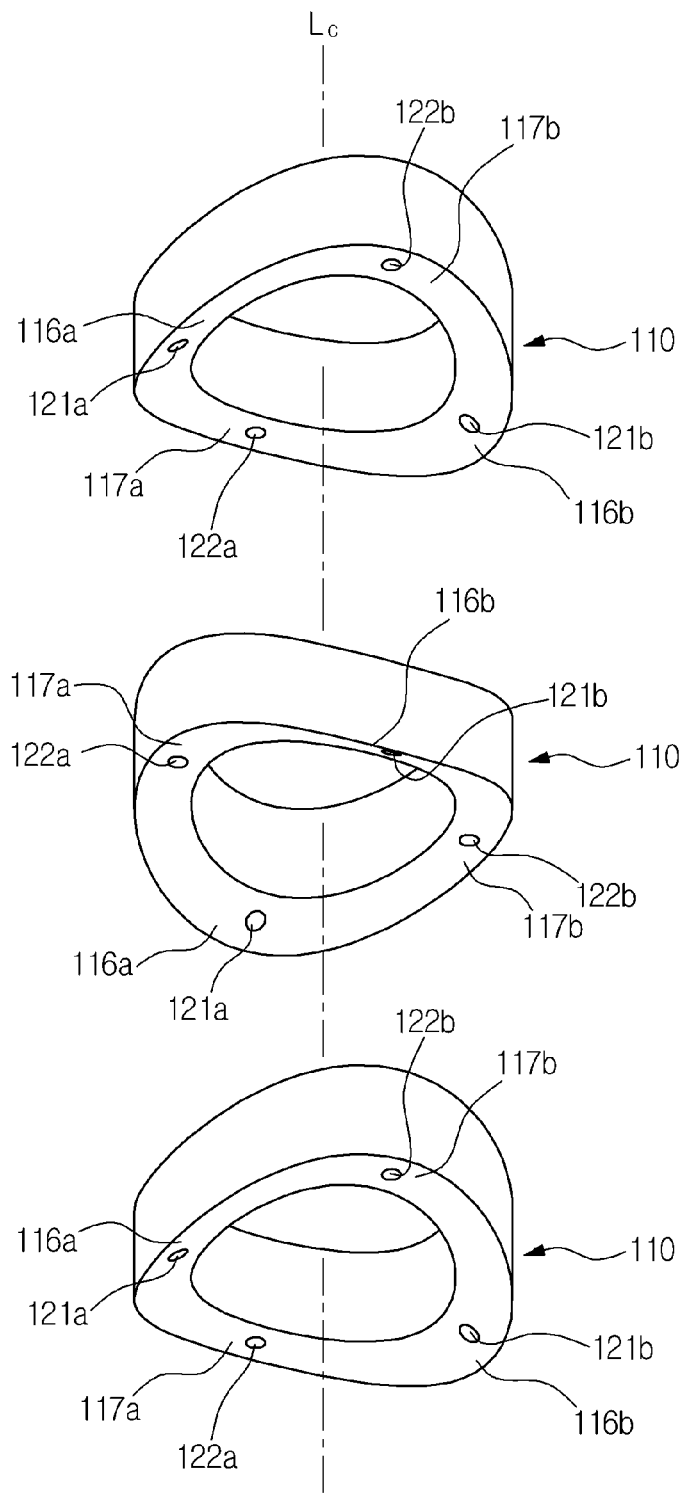
[FIG. 3]

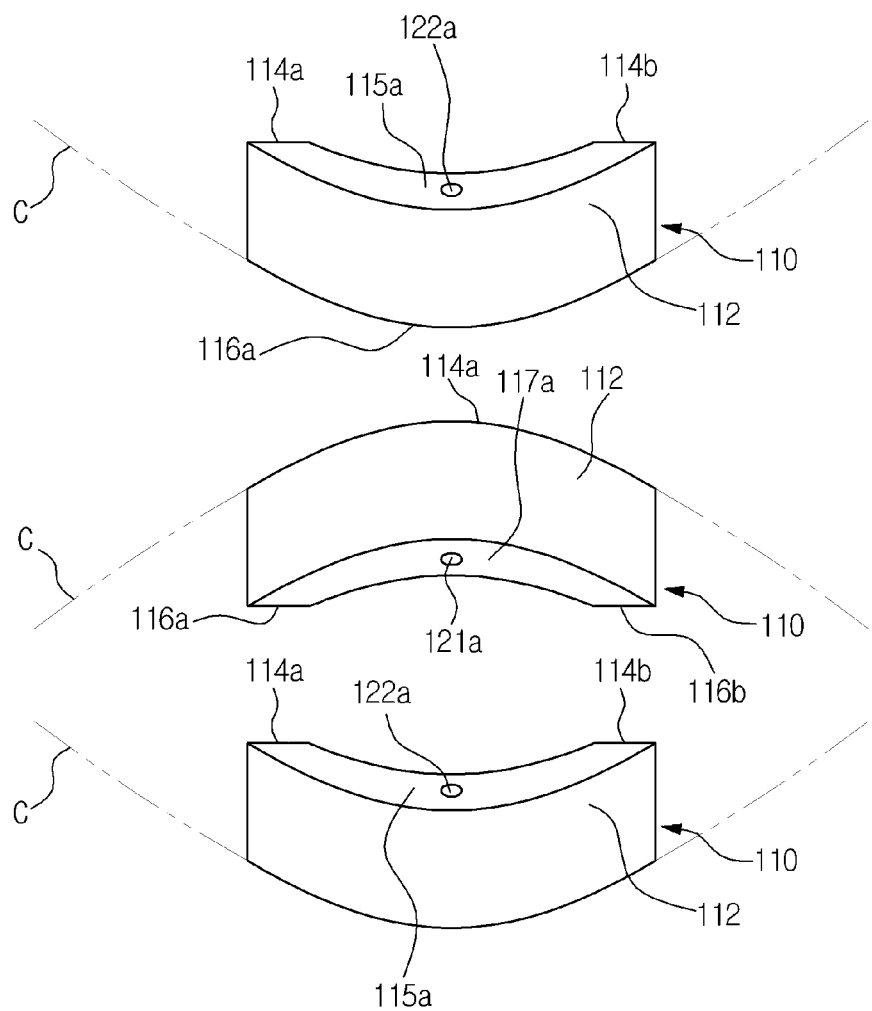
[FIG. 4]

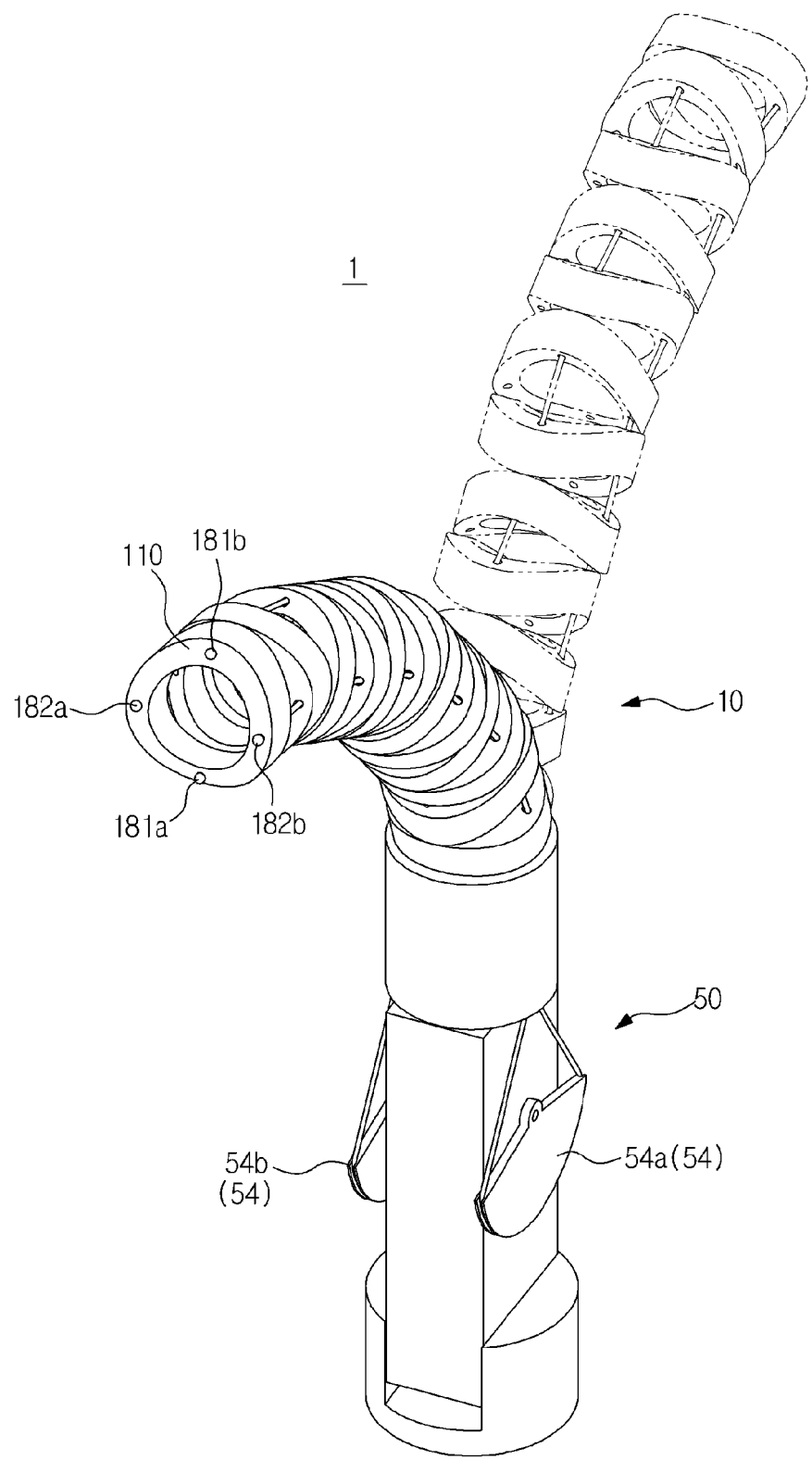
[FIG. 5A]

[FIG. 5B]
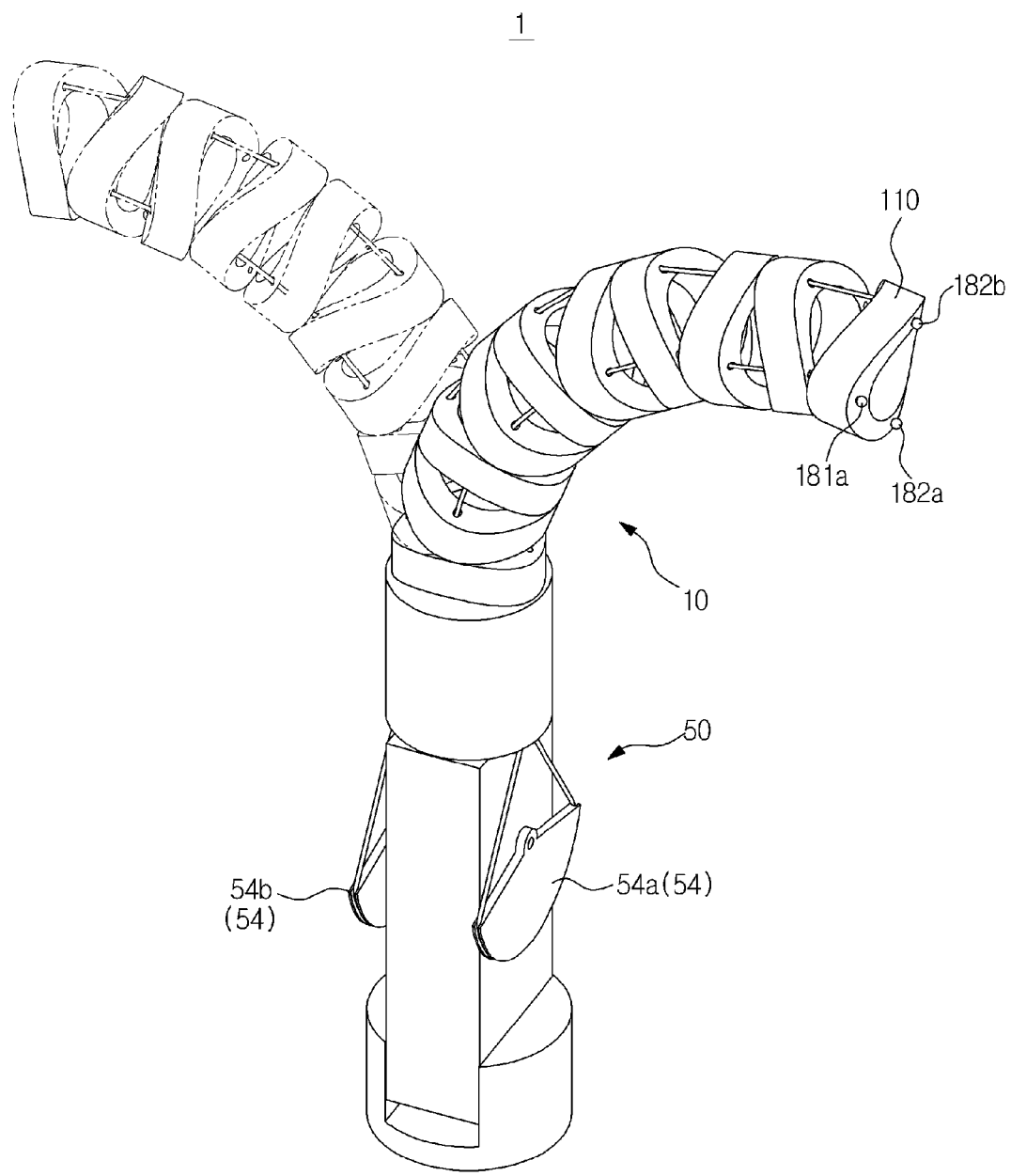

[FIG. 6A]
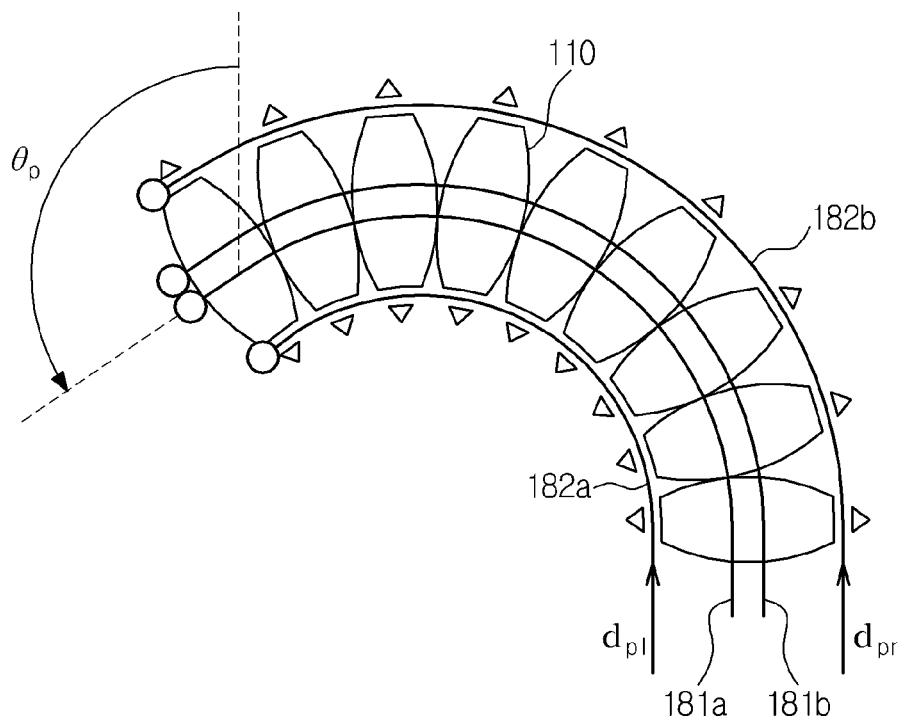

[FIG. 6B]
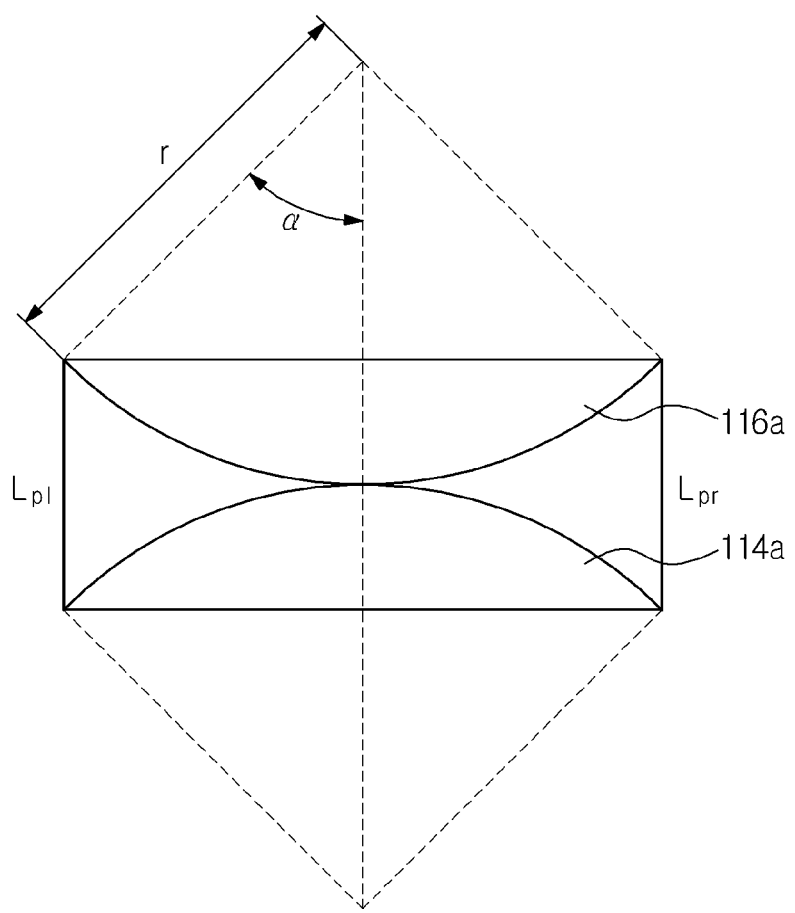

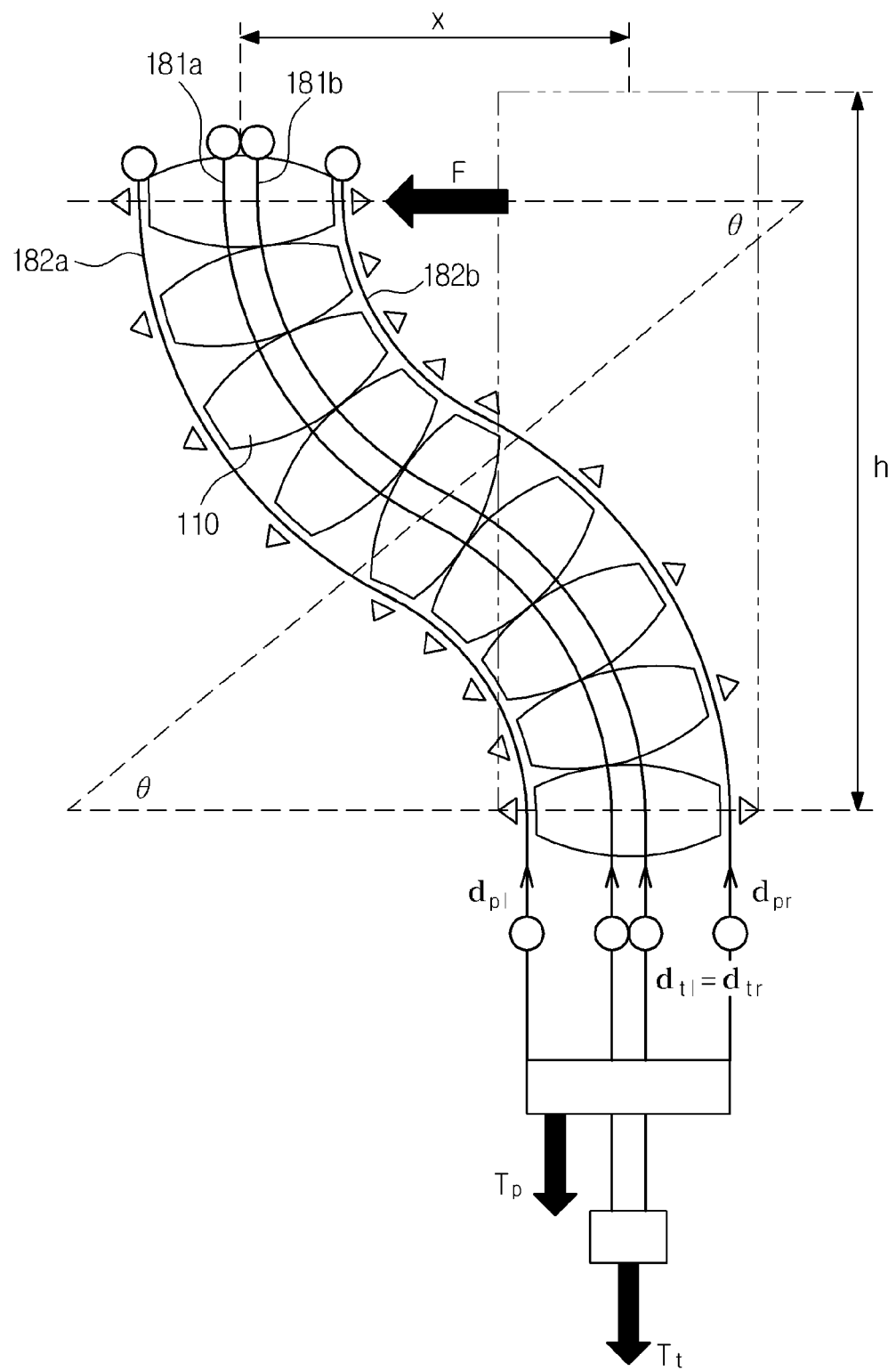
[FIG. 7A]

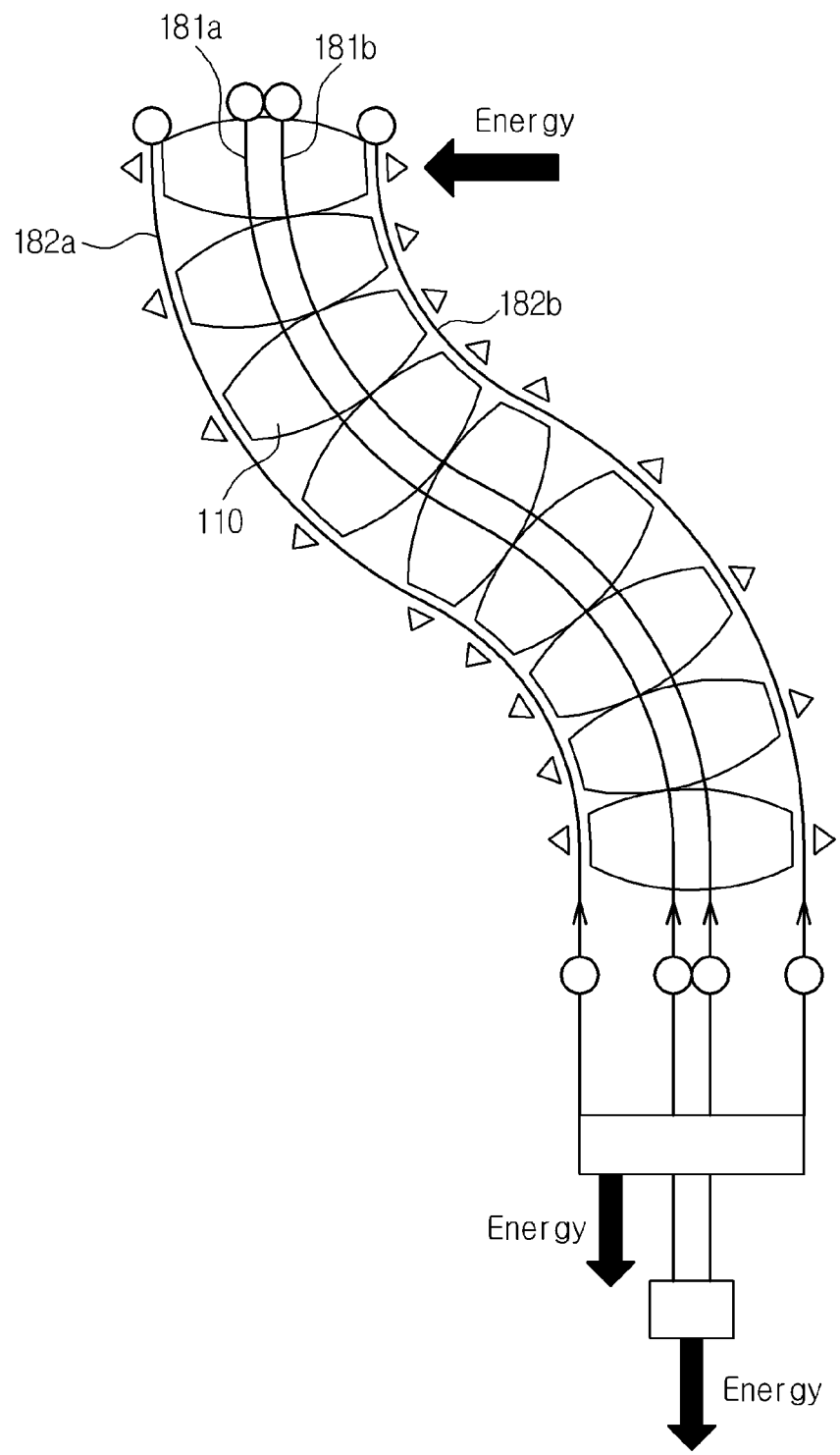

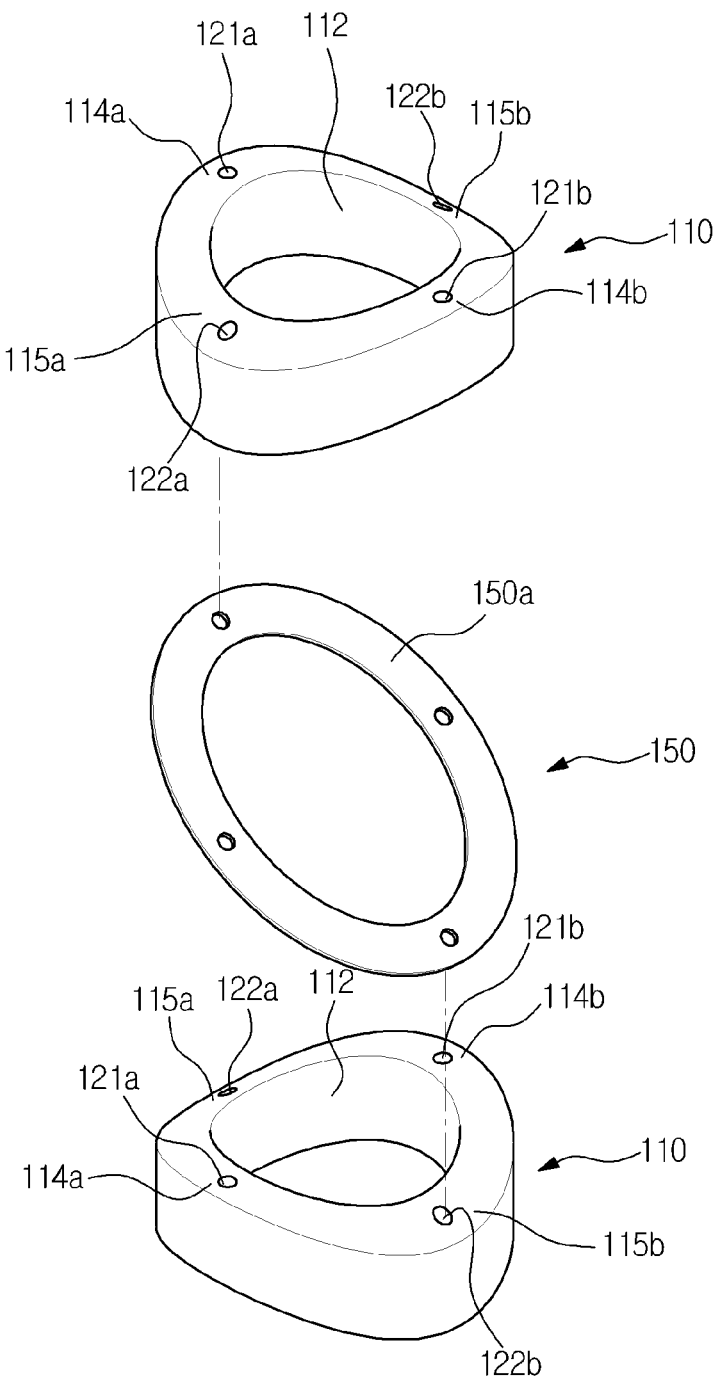

[FIG. 8B]
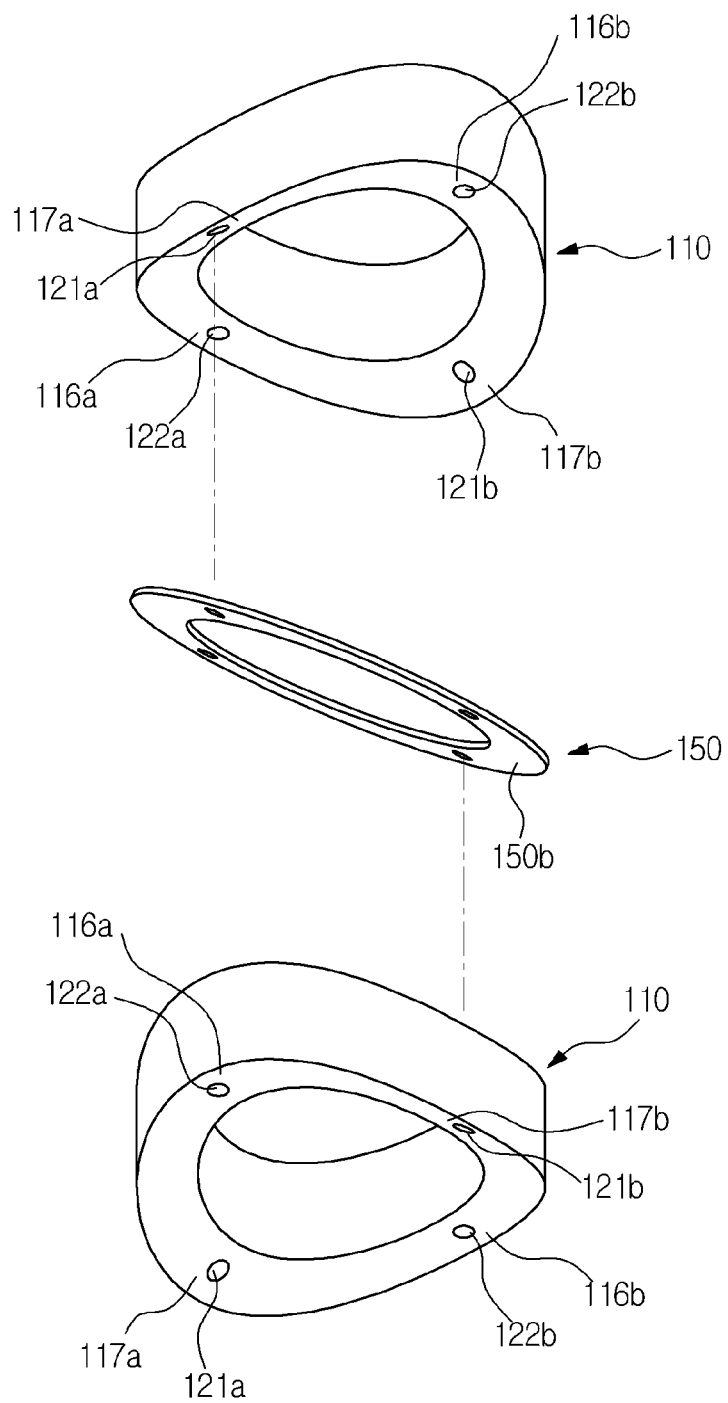

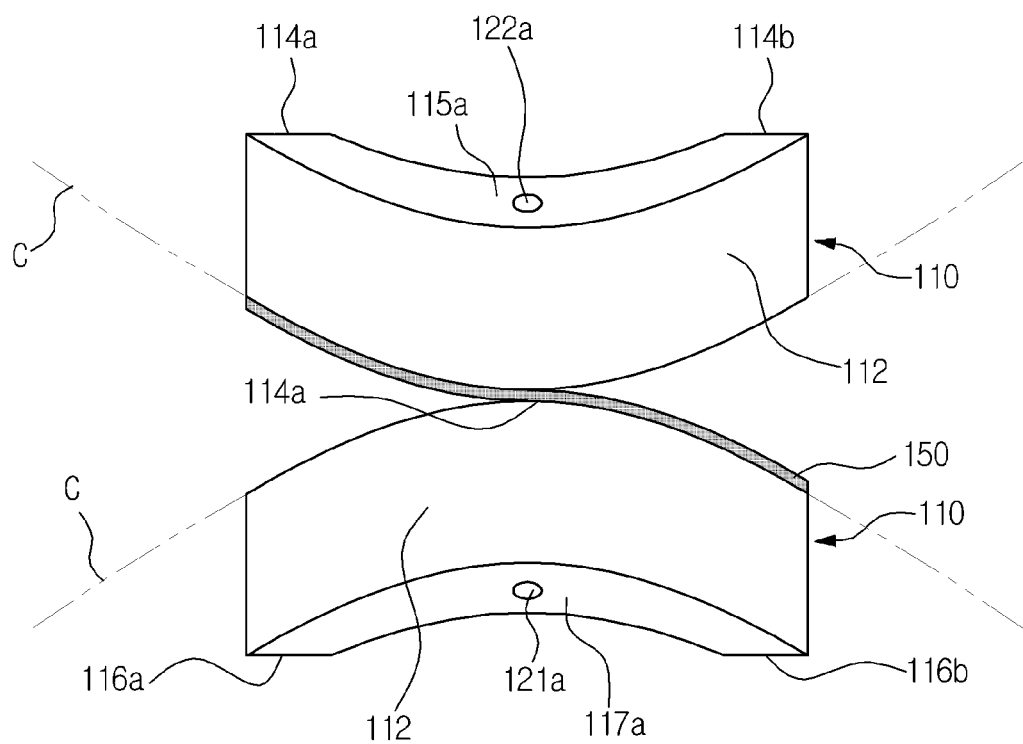
[FIG. 8C]

[FIG. 9A]
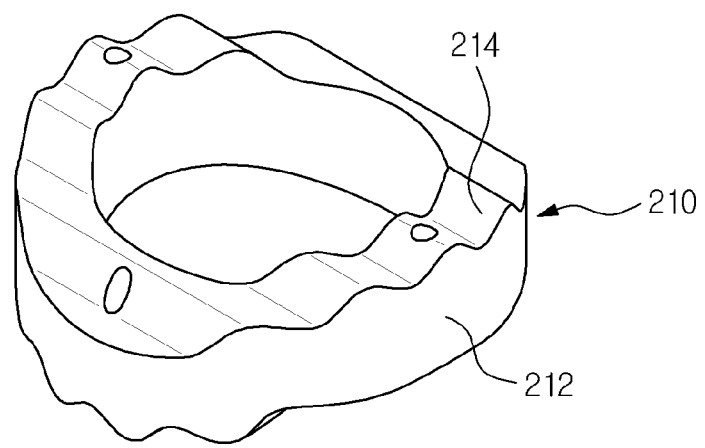
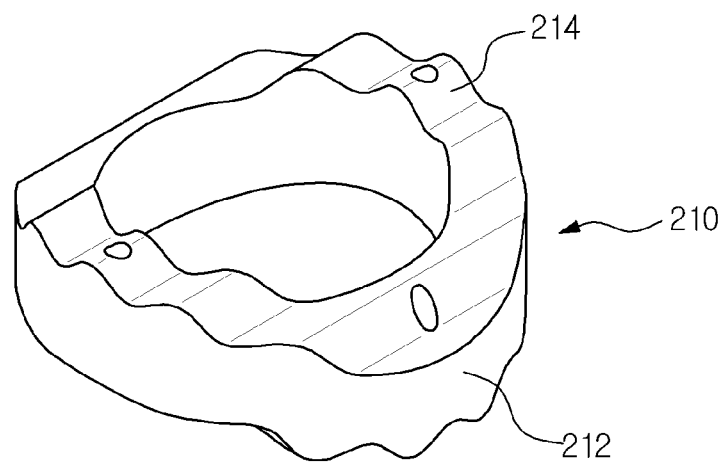

[FIG. 9B]
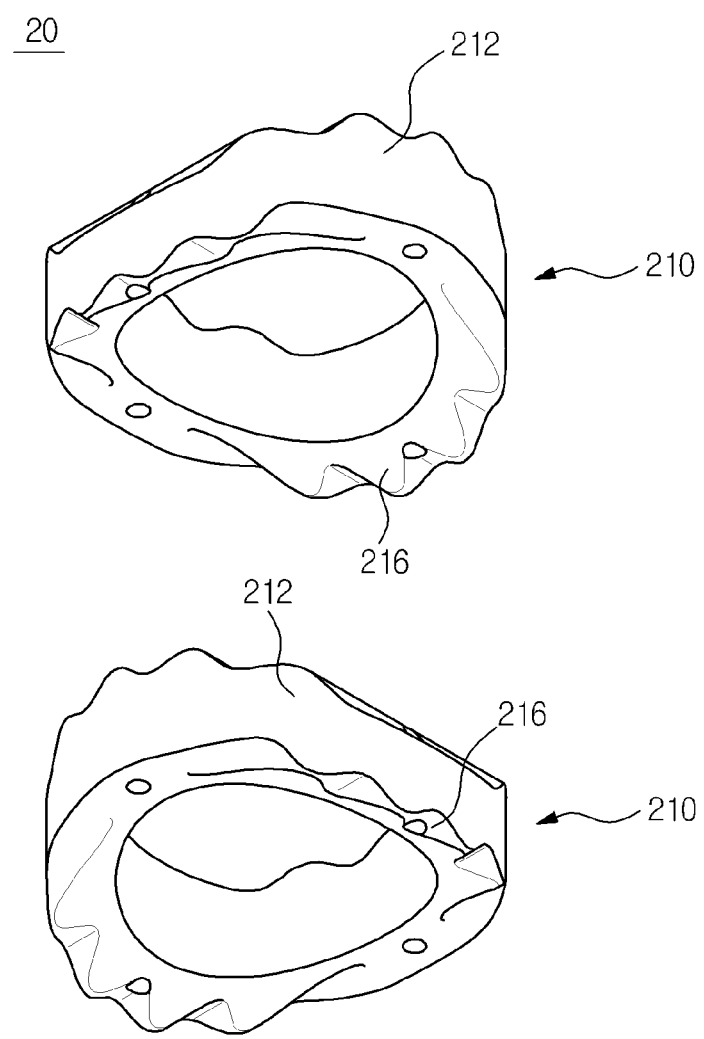

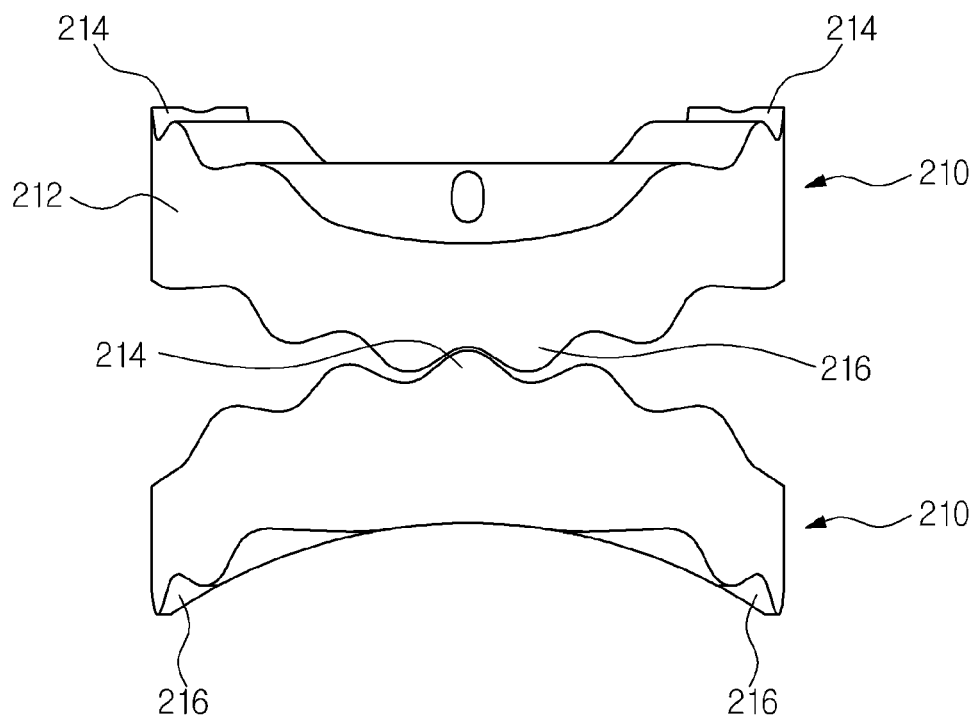
[FIG. 9C]

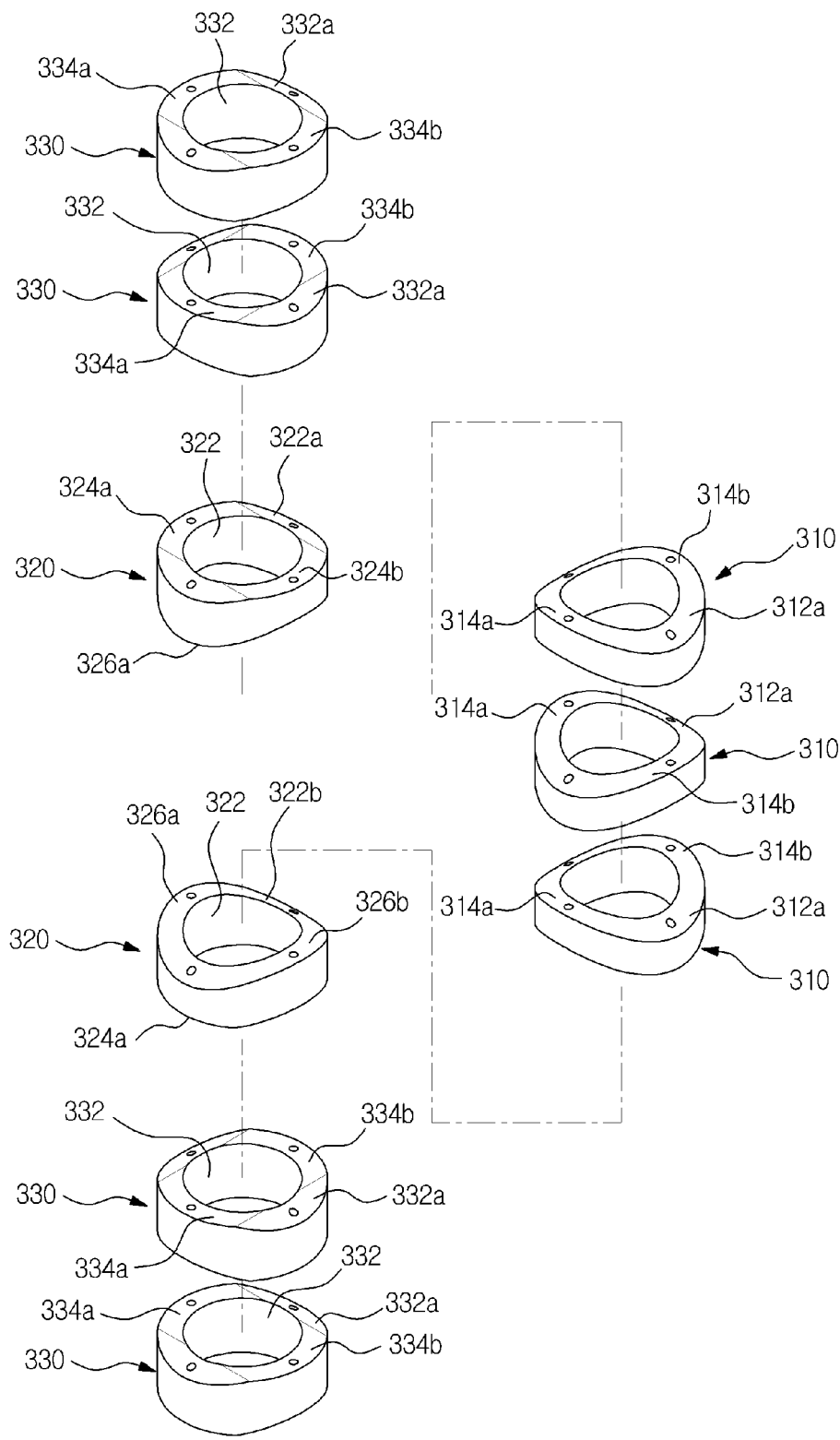
[FIG. 10A]

【FIG. 10B】
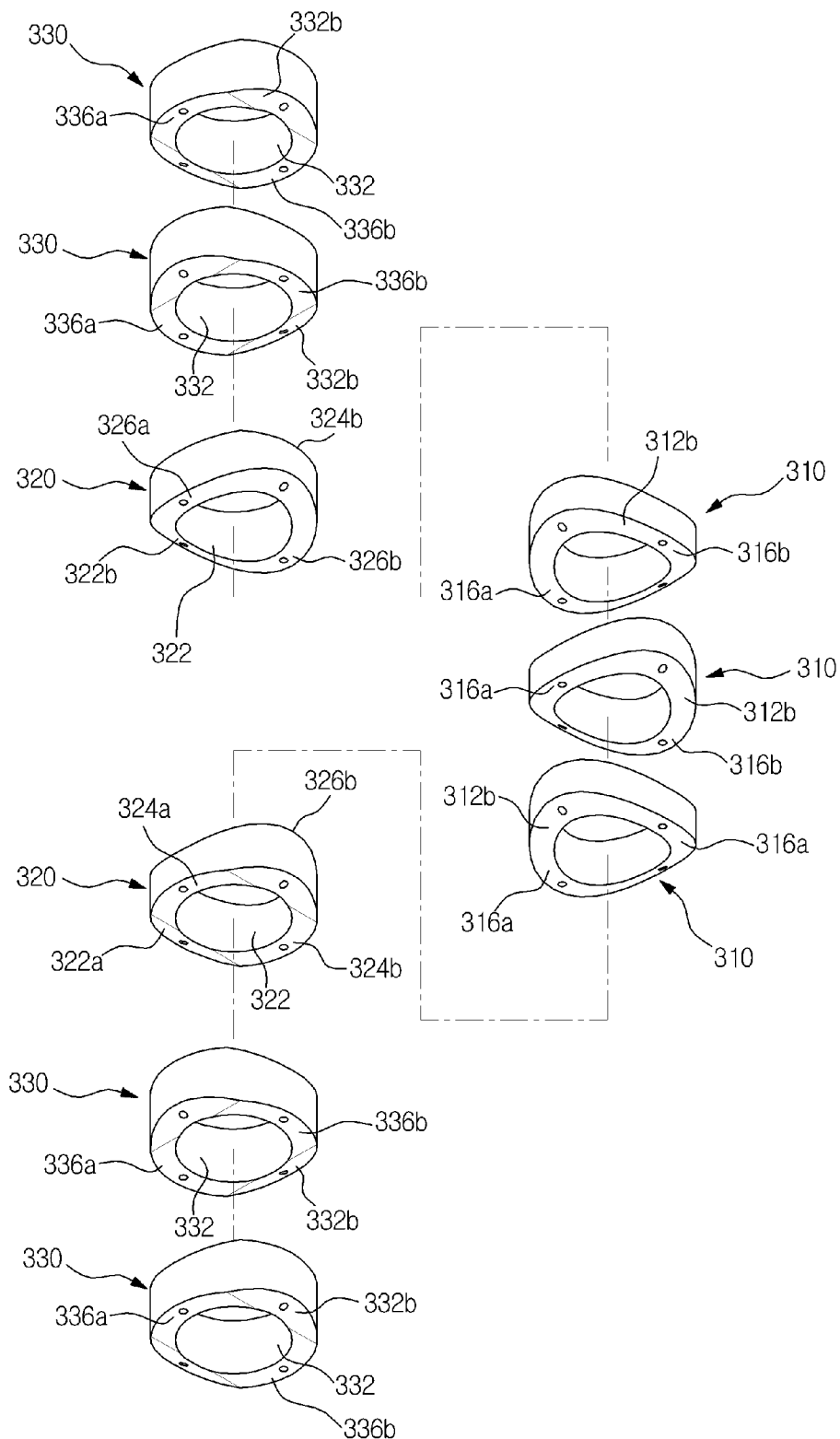

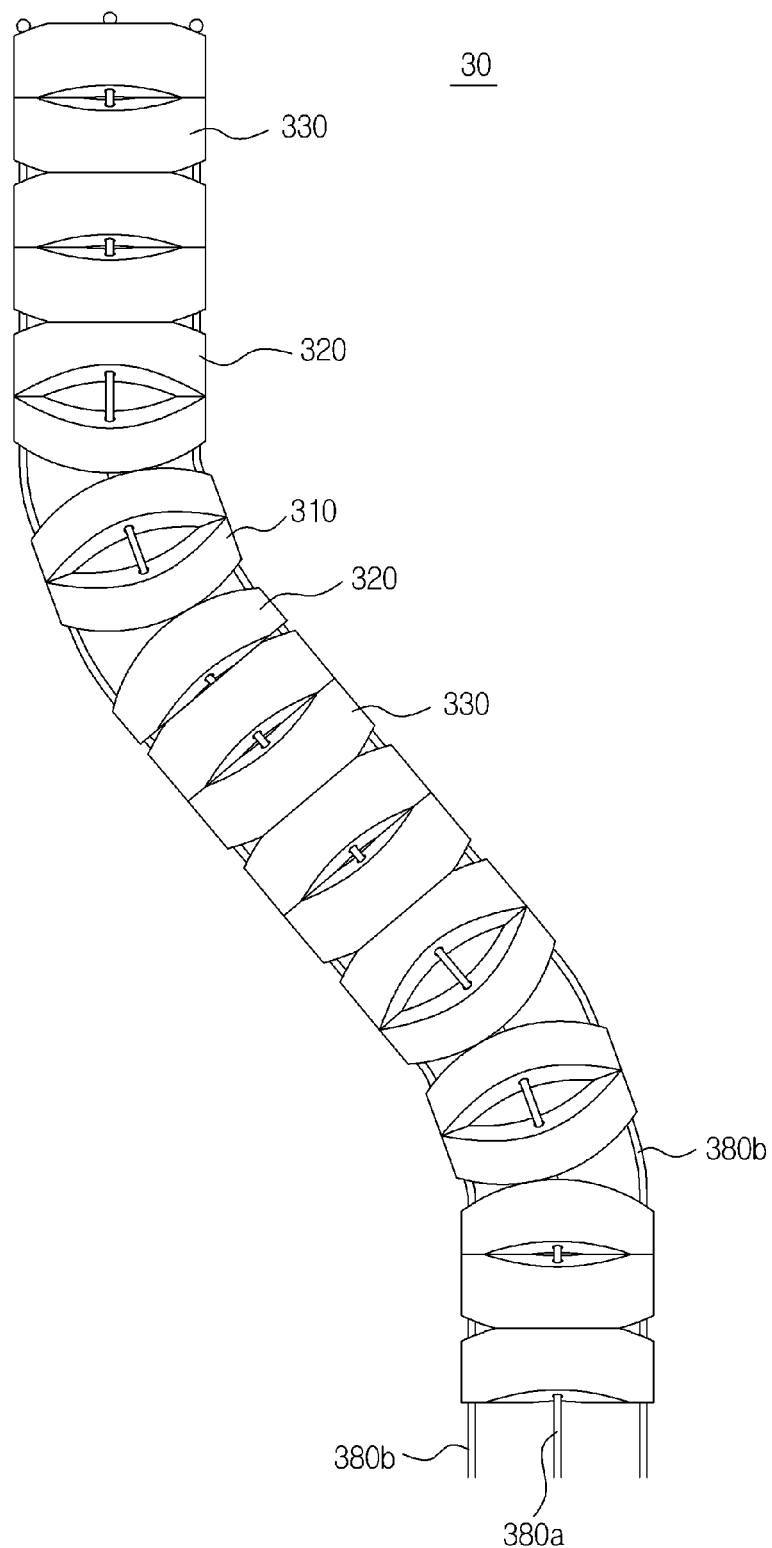
[FIG. 10C]

[FIG. 11A]
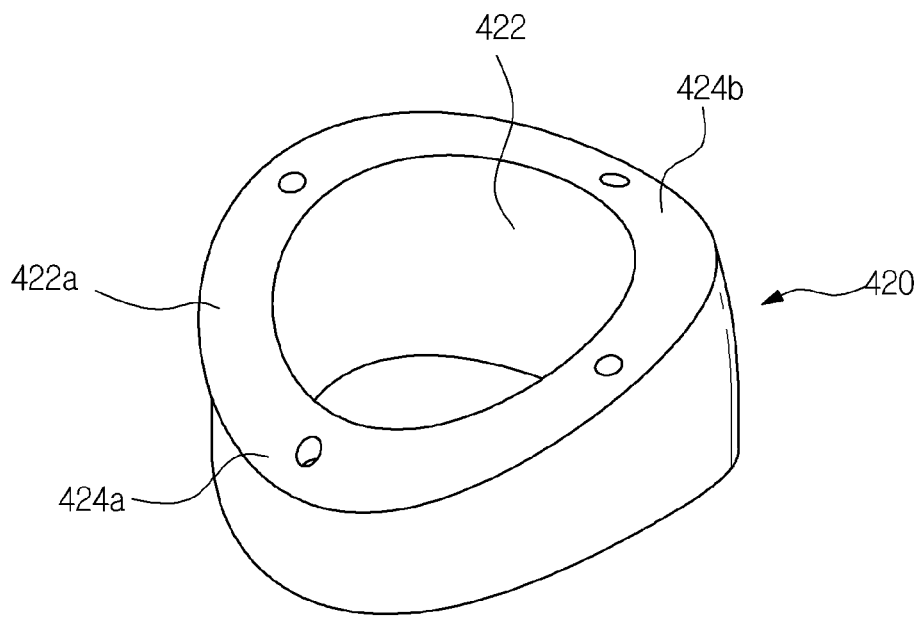
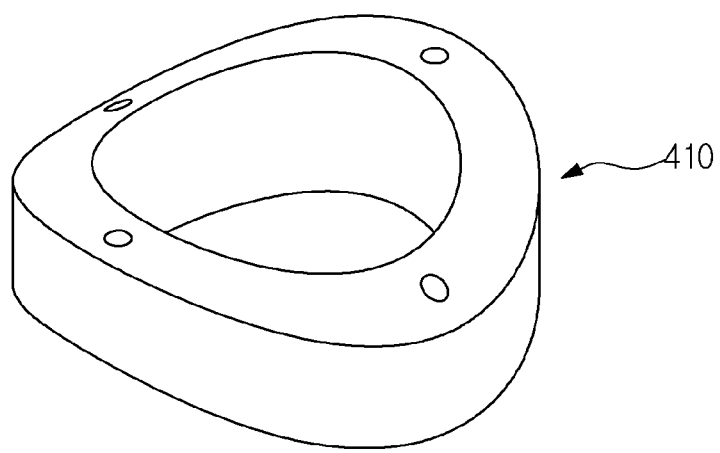

[FIG. 11B]
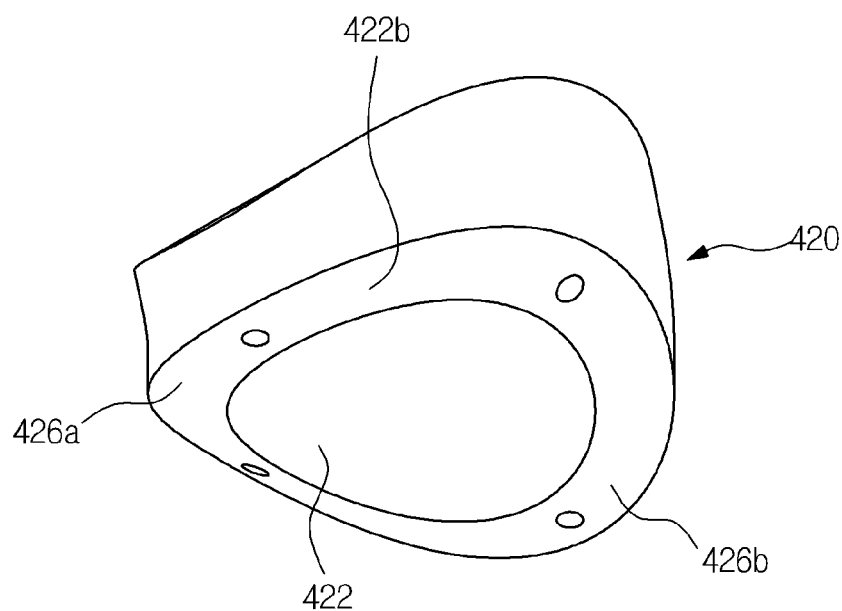
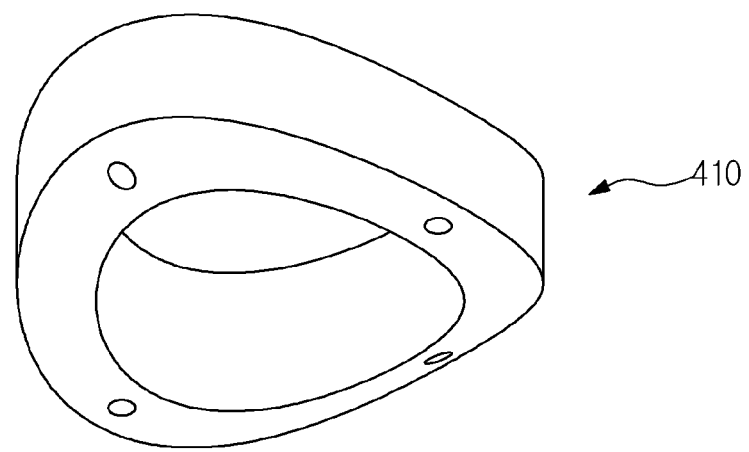

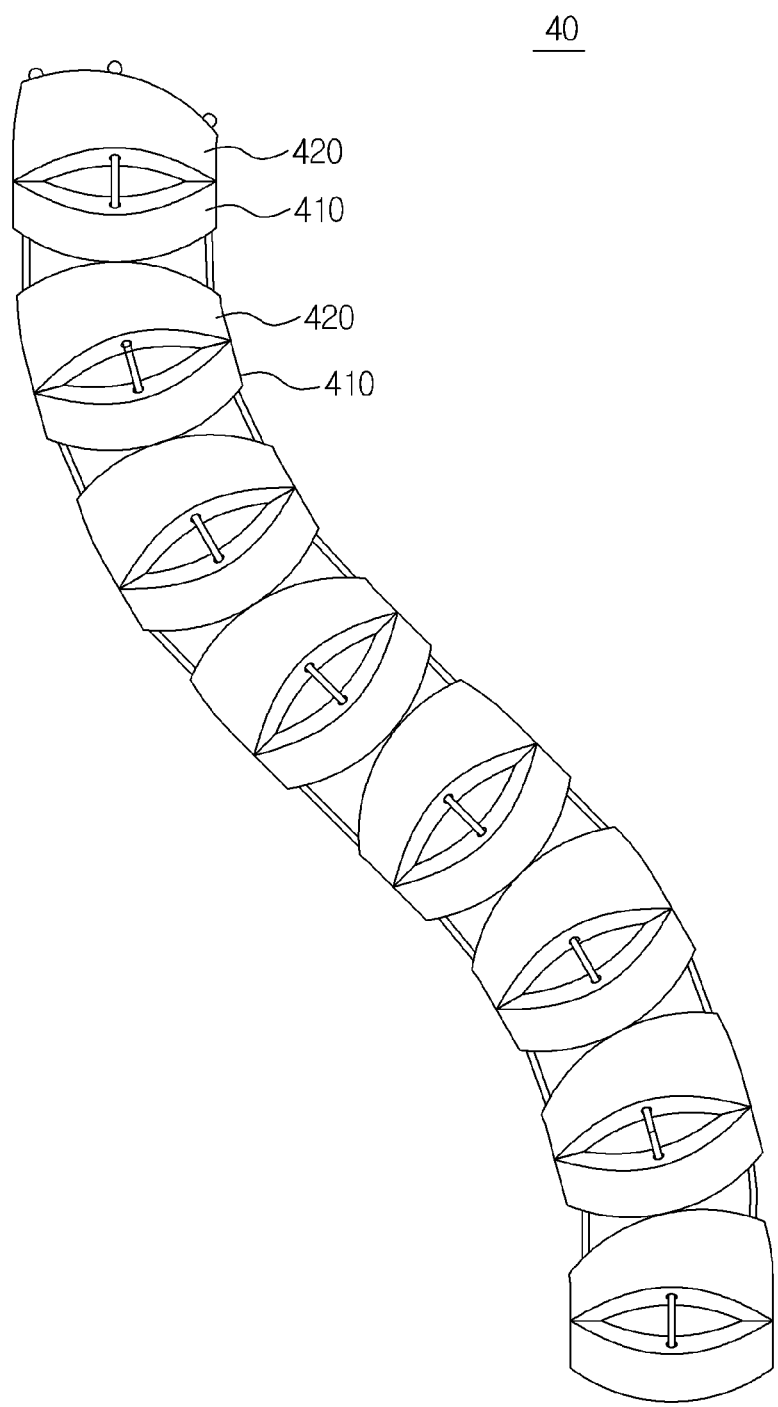
[FIG. 11C]

ARM UNIT AND ROBOT HAVING THE SAME

CROSS-REFERENCE TO RELATED APPLICATIONS

This application claims the benefit of Korean Patent Applications No. 2012-0056374, filed on May 25, 2012 and No. 2012-0131721, filed on Nov. 20, 2012 in the Korean Intellectual Property Office, the disclosures of which are incorporated herein by reference.

BACKGROUND

1. Field

One or more embodiments of the present disclosure relate to an arm unit and a robot having the same.

2. Description of the Related Art

Minimally invasive surgery refers to surgical methods less invasive than open surgeries, and a representative example of minimally invasive surgery is laparoscopic surgery. In contrast with existing laparotomy using surgical incisions through the abdominal wall, in minimally invasive surgery, after preparing a surgery space in the abdomen by injecting gas through several small ports, an operator inserts a laparoscope and a surgical manipulator through the ports, to perform surgery using the manipulator while viewing laparoscopic images.

As compared to laparotomy, laparoscopic surgery has several advantages, such as low pain after surgery, short hospitalization, rapid return to daily life, and superior cosmetic effects owing to a smaller incision. However, the surgical manipulator can be difficult to control and is designed only for movement through the ports.

To compensate for the aforementioned disadvantages of laparoscopic surgery, single port surgery or Natural Orifice Translumenal Endoscopic Surgery (NOTES), which performs surgery by inserting the surgical manipulator through a natural orifice, such as the mouth, urethra, and anus, without forming any one port has recently been studied.

To efficiently perform single port surgery or NOTES, an arm of the surgical manipulator may require flexibility to pass along curved internal organs of a patient as well as stiffness to endure any load applied to a surgical part.

SUMMARY

It is an aspect of the present disclosure to provide an arm unit having an improved configuration to simply change stiffness according to situations and a robot having the same.

Additional aspects of the disclosure will be set forth in part in the description which follows and, in part, will be obvious from the description, or may be learned by practice of the disclosure.

In accordance with one aspect of the disclosure, a robot includes an arm unit, and a drive unit to drive the arm unit, wherein the arm unit includes a plurality of links to come into rolling contact with one another via at least two regions thereof, and a plurality of wires penetrating the plurality of links to connect the links to one another.

The plurality of links may be arranged in series, and at least two links among the plurality of links may come into rolling contact with neighboring links.

At least one link among the plurality of links may include a centrally-hollowed body, and a plurality of first rolling-contact portions of the body curved in a first direction facing another neighboring link.

Each of the plurality of links may include a plurality of second rolling-contact portions of the body curved in a second direction opposite to the first direction.

The plurality of first rolling-contact portions may include a pair of first rolling-contact portions arranged at 180°-rotated positions on the basis of a center axis of the body in a longitudinal direction of the body.

The plurality of second rolling-contact portions may include a pair of second rolling-contact portions arranged at 180°-rotated positions on the basis of the center axis of the body in a longitudinal direction of the body.

The first rolling-contact portions may be arranged at 90°-rotated positions with respect to the second rolling-contact portions on the basis of the center axis of the body in a circumferential direction of the body.

The first rolling-contact portion may include a rolling-contact surface coming into rolling contact with another neighboring link.

At least a part of the first rolling-contact portion may be a part of a circle having a predetermined curvature.

The plurality of links may include a first link, and a second link to come into rolling contact with an upper surface or a lower surface of the first link at a 90°-rotated position with respect to the first link on the basis of a center axis penetrating the center of the first link in a longitudinal direction of the body.

The robot may further include an anti-slip member located between the first link and the second link to prevent slip between the first link and the second link.

One surface of the anti-slip member may come into contact with a part of the first link, and the other surface may come into contact with a part of the second link.

A first surface of the first link opposite to the second link and a second surface of the second link coming into rolling contact with the first surface may be respectively provided with a first toothed portion and a second toothed portion, which are engaged with each other to prevent slip between the first link and the second link.

The first toothed portion may be circumferentially formed at the first surface of the first link having a centrally-hollowed shape, and the second toothed portion may be circumferentially formed at the second surface of the second link having a centrally-hollowed shape.

The first rolling-contact portions may have different heights.

The plurality of links may include a first link having upper and lower surfaces, all of which come into rolling contact with other neighboring links, a second link having upper and lower surfaces, one of which comes into rolling contact with another neighboring link, and the other one of which comes into surface contact with another neighboring link, and at least one third link having upper and lower surfaces, all of which come into surface contact with other neighboring links.

The second link may be located between the first link and the third link.

The at least one third link may include at least two third links arranged neighboring each other to serve as rigid bodies during driving of the arm unit.

The plurality of wires may include a pair of first wires penetrating the first rolling contact portions in an arrangement direction of the plurality of links, and a pair of second wires penetrating the second rolling contact portions in an arrangement direction of the plurality of links.

An extension length of any one of the pair of first wires may be non-symmetric to a contraction length of the other one during driving of the arm unit.

Tension applied to the first wire and the second wire may be proportional to stiffness of the arm unit.

The drive unit may include at least one pulley to change paths of first and second wires, and drive plates connected respectively to the first and second wires to adjust tension applied to the first and second wires.

In accordance with another aspect of the present disclosure, in a robot including an arm unit having a plurality of links and a drive unit to drive the arm unit, each of the links includes a centrally-hollowed body, and at least one convex portion raised in a longitudinal direction of the body from a part of at least one of an upper surface and a lower surface of the body so as to come into rolling contact with another neighboring link.

The link may include at least one concave portion connected to the convex portion, and the concave portion may define a pivoting space to allow one link and another link neighboring each other to pivot relative to each other via the convex portions thereof.

The at least one convex portion may include a pair of convex portions arranged opposite to each other on the basis of an imaginary first division plane including a center axis of the body.

The at least one concave portion may include a pair of concave portions arranged opposite to each other on the basis of an imaginary second division plane perpendicular to the first division plane.

The convex portion may include a rolling contact surface to come into rolling contact with another neighboring link, and at least a part of the rolling contact surface may be a part of a circle having a predetermined curvature.

The plurality of links may include a first link, and second and third links having the same shape as the first link and arranged respectively neighboring an upper surface and a lower surface of the first link, the first link may include a centrally-hollowed body, a pair of first convex portions longitudinally raised from a part of an upper surface of the body to come into rolling contact with the second link, and a pair of second convex portions raised from a part of a lower surface of the body in a direction opposite to the raised direction of the first convex portions to come into rolling contact with the third link, and the second convex portions may be located at 90°-rotated positions with respect to the first convex portions on the basis of a center axis of the body in a longitudinal direction of the body.

The second link may include a centrally-hollowed body, a pair of third convex portions longitudinally raised from a part of an upper surface of the body to come into rolling contact with another link neighboring an upper surface of the second link, and a pair of fourth convex portions raised from a part of a lower surface of the body in a direction opposite to the raised direction of the first convex portions to come into rolling contact with the first link, and the pair of fourth convex portions may respectively comes into rolling contact with the pair of first convex portions.

The robot may further include an anti-slip member located between the first link and the second link to prevent slip between the first link and the second link, one surface of the anti-slip member may come into contact with the first convex portions, and the other surface may come into contact with the fourth convex portions.

The first convex portions and the fourth convex portions may include toothed portions to allow at least a part of the first convex portions and at least a part of the fourth convex portions to engage with each other, to prevent slip between the first link and the second link.

Each of the pair of convex portions may be raised by different lengths.

In accordance with one aspect of the disclosure, a robot arm includes a plurality of links to come into rolling contact with one another via a plurality of convex portions of the links and a plurality of wires penetrating the links to couple the links to one another.

In accordance with one aspect of the disclosure, a robot arm includes a plurality of links sequentially coupled to one another in a rolling-contact manner and a plurality of wires penetrating the links to couple the links to one another. Each link of the robot arm includes a pair of first rolling-contact portions formed by curving an upper surface of the link in a first direction toward another link disposed directly above the link, and a pair of second rolling-contact portions formed by curving a lower surface of the link in a direction opposite to the first direction In accordance with one aspect of the disclosure, a robot arm includes a plurality of links sequentially coupled to each other in a rolling contact manner and a plurality of wires penetrating the links to connect the links to one another. The plurality of links include a first link including a pair of first convex portions formed by curving a first portion of an upper surface of the first link in a first direction toward a link disposed directly above the first link, and a pair of first concave portions formed by curving a second portion of the upper surface of the first link in a direction opposite to the first direction and a second link including a pair of second convex portions formed by curving a first portion of a lower surface of the second link body in the first direction toward the first link, and a pair of second concave portions formed by curving a second portion of the lower surface of the second link body in the direction opposite to the first direction. A first wire of the plurality of wires penetrates a hole disposed in one of the pair of first convex portions of the first link and penetrates a hole disposed in one of the pair of second convex portions of the second link thereby connecting the first link and the second link to form an articulated portion of the robot arm.

In accordance with one aspect of the disclosure, a robot arm includes a plurality of links sequentially coupled to each other in a rolling contact manner and a plurality of wires penetrating the links to connect the links to one another. The plurality of links includes a first link including a centrally-hollowed body, a pair of first convex portions formed by curving a first portion of an upper surface of the first link body in a first direction toward a link disposed directly above the first link, and a pair of first concave portions formed by curving a second portion of the upper surface of the first link body in a direction opposite to the first direction and a second link including the centrally-hollowed body, a pair of second convex portions formed by curving a lower surface of a first portion of the second link body in the first direction toward the first link, and a pair of second concave portions formed by curving a second portion of the lower surface of the second link body in the direction opposite to the first direction. A first wire of the plurality of wires penetrates a hole disposed in one of the pair of first convex portions and penetrates a hole disposed in one of the pair of second convex portions of the second link thereby connecting the first link and the second link to form an articulated portion of the robot arm. A second wire of the plurality of wires penetrates a hole disposed in one of the pair of first concave portions of the first link and penetrates a hole disposed in one of the pair of second concave portions of the second link thereby further connecting the first link and the second link.

BRIEF DESCRIPTION OF THE DRAWINGS

These and/or other aspects of the disclosure will become apparent and more readily appreciated from the following description of the embodiments, taken in conjunction with the accompanying drawings of which:

FIG. 1 is a view illustrating an arm unit and a drive unit according to an embodiment;

FIG. 2 is a view illustrating links constituting the arm unit of FIG. 1;

FIG. 3 is a view illustrating the links of FIG. 2 when viewed from a different angle;

FIG. 4 is a side view of FIG. 2;

FIGS. 5A and 5B are views illustrating a tilt motion and a pan motion of the arm unit according to an embodiment;

FIGS. 6A, 6B, 7A and 7B are views explaining a relationship between tension applied to wires and stiffness of the arm unit;

FIGS. 8A, 8B and 8C are views illustrating insertion of an anti-slip member through the links constituting the arm unit according to an embodiment;

FIGS. 9A, 9B and 9C are views illustrating an arm unit according to another embodiment;

FIGS. 10A, 10B and 10C are views illustrating an arm unit according to another embodiment; and FIGS. 11A, 11B and 11C are views illustrating an arm unit according to a further embodiment.

DETAILED DESCRIPTION

Reference will now be made in detail to the embodiments of the present disclosure, examples of which are illustrated in the accompanying drawings, wherein like reference numerals refer to like elements throughout.

FIG. 1 is a view illustrating an arm unit and a drive unit according to an embodiment.

As illustrated in FIG. 1, a robot 1 may include, for example, an arm unit 10, and a drive unit 50 to drive the arm unit 10.

The arm unit 10 may include links 110 arranged in series in a rolling contact manner, and wires 181a, 181b, 182a and 182b penetrating the links 110 to connect the links 110 to one another.

The wires 181a, 181b, 182a and 182b include a pair of first wires 181a and 181b arranged opposite to each other to realize a tilt motion of the arm unit 10, and a pair of second wires 182a and 182b arranged opposite to each other to realize a pan motion of the arm unit 10.

The drive unit 50 includes at least one pulley 52 to change paths of the wires 181a, 181b, 182a and 182b, drive plates 54 connected to the wires 181a, 181b, 182a and 182b to adjust tension applied to the wires 181a, 181b, 182a and 182b, and a drive motor (not shown) to drive the drive plates 54.

The drive plates 54 have an arc shape such that the wires 181a, 181b, 182a and 182b are wound on the drive plates 54. The drive plates 54 include a first drive plate 54a that is connected to the first wires 181a and 181b associated with a tilt motion of the arm unit 10 to adjust tension of the first wires 181a and 181b, and a second drive plate 54b that is connected to the second wires 182a and 182b associated with a pan motion of the arm unit 10 to adjust tension of the second wires 182a and 182b.

The first drive plate 54a and the second drive plate 54b are individually rotated, thereby adjusting tension of the first wires 181a and 181b and the second wires 182a and 182b to realize a tilt motion and a pan motion of the arm unit 10.

FIG. 2 is a view illustrating the links making up the arm unit of FIG. 1, FIG. 3 is a view illustrating the links of FIG. 2 when viewed from a different angle, FIG. 4 is a side view of FIG. 2, and FIGS. 5A and 5B are views illustrating a tilt motion and a pan motion of the arm unit according to an embodiment.

As illustrated in FIGS. 2 to 5B, each link 110 includes a centrally-hollowed body 112, a pair of first rolling-contact portions 114a and 114b formed by curving a surface of the body 112 in a first direction toward another neighboring link 110 disposed above the link 110, and a pair of second rolling-contact portions 116a and 116b formed by curving a surface of the body 112 in a direction opposite to the first direction.

The first rolling-contact portions 114a and 114b are longitudinally raised from a part of an upper surface of the body 112, so as to come into contact with another neighboring link 110 disposed above link 110. The second rolling-contact portions 116a and 116b are raised from a part of a lower surface of the body 112 in a direction opposite to the raised direction of the first rolling-contact portions 114a and 114b, so as to come into contact with another neighboring link 110 disposed below link 110. That is, the first rolling-contact portions 114a and 114b and the second rolling-contact portions 116a and 116b may be respectively referred to as first convex portions 114a and 114b and second convex portions 116a and 116b.

The pair of first rolling-contact portions 114a and 114b or the pair of second rolling-contact portions 116a and 116b may be arranged at 180°-rotated positions on the basis of a center axis Lc of the body 112 in a longitudinal direction of the body. That is, in an embodiment, the pair of first rolling-contact portions 114a and 114b or the pair of second rolling-contact portions 116a and 116b may be disposed opposite to each other on the body as illustrated, for example, at FIG. 2. Also, the pair of first rolling-contact portions 114a and 114b may be arranged at 90°-rotated positions with respect to the pair of second rolling-contact portions 116a and 116b on the basis of the center axis Lc in a circumferential direction of the body 112.

The upper surface of the body 112, on which the first rolling-contact portions 114a and 114b are formed, is provided with first concave portions 115a and 115b connected to the first rolling-contact portions 114a and 114b. The lower surface of the body 112, on which the second rolling-contact portions 116a and 116b are formed, is provided with second concave portions 117a and 117b connected to the second rolling-contact portions 116a and 116b. The first concave portions 115a and 115b are arranged at 90°-rotated positions with respect to the first rolling-contact portions 114a and 114b on the basis of the center axis Lc in a circumferential direction of the body 112. The second concave portions 117a and 117b are arranged at 90°-rotated positions with respect to the second rolling-contact portions 116a and 116b on the basis of the center axis Lc in a circumferential direction of the body 112. The first rolling-contact portions 114a and 114b are arranged symmetrically to each other on the basis of an imaginary first division plane F1 containing the center axis Lc, and the first concave portions 115a and 115b are arranged symmetrically to each other on the basis of an imaginary second division plane F2 that contains the center axis Lc and is perpendicular to the first division plane F1, as illustrated at FIG. 2.

The pair of first rolling-contact portions 114a and 114b and the pair of second rolling-contact portions 116a and 116b respectively have first through-holes 121a and 121b and second through-holes 122a and 122b for penetration of the first wires 181a and 181b and the second wires 182a and 182b to realize a tilt motion and a pan motion.

The individual links 110 are sequentially coupled to one another such that each link 110 is rotated by 90° on the basis of the center axis Lc with respect to another neighboring link 110, thereby constituting or articulating the arm unit 10. Thereby, as illustrated in FIG. 1, the first wires 181a and 181b and the second wires 182a and 182b respectively penetrate the first through-holes 121a and 121b of one link 110 and the second through-holes 122a and 122b of another neighboring link 110 in sequence.

To enable relative pivoting of the respective neighboring links 110, at least a part of each of the first and second rolling-contact portions 114a and 114b and 116a and 116b may be a part of a circle having a predetermined curvature C as illustrated in FIG. 4. Thus, in an embodiment, the phrase "rolling contact manner" may describe rolling-contact portions rotating with respect to each other while making contact along curvature C to thereby enable relative pivoting of the respective neighboring links 110.

In a state in which no force is applied to the wires 181a, 181b, 182a and 182b, the first rolling-contact portions 114a and 114b formed at the upper surface of the body 112 of any one link 110 come into rolling contact with the second rolling-contact portions 116a and 116b formed at the lower surface of the body 112 of another link 110 located thereabove, and the second rolling-contact portions 116a and 116b formed at the lower surface of the body 112 of any one link 110 come into rolling contact with the first rolling-contact portions 114a and 114b formed at the upper surface of the body 112 of another link 110 located therebelow.

The first concave portions 115a and 115b, which are connected to the first rolling-contact portions 114a and 114b of any one link 110, are arranged opposite to the second concave portions 117a and 117b, which are connected to the second rolling-contact portions 116a and 116b of another link 110 located thereabove. With this arrangement, pivoting spaces S1 and S2 are defined to enable relative pivoting of the respective neighboring links 110, as illustrated at FIG. 1, for example. Also, the second concave portions 117a and 117b, which are connected to the second rolling-contact portions 116a and 116b of any one link 110, are arranged opposite to the first concave portions 115a and 115b, which are connected to the first rolling-contact portions 114a and 114b of another link 110 located therebelow, defining pivoting spaces S1 and S2.

As illustrated in FIG. 5A, when adjusting tension of the first wires 181a and 181b, relative pivoting between the second rolling-contact portions 116a and 116b formed at the lower surface of the body 112 of any one link 110 and the first rolling-contact portions 114a and 114b formed at the upper surface of the body 112 of another link 110 occurs, whereby a tilt motion is realized.

Also, as illustrated in FIG. 5B, when adjusting tension of the second wires 182a and 182b, relative pivoting between the first rolling-contact portions 114a and 114b formed at the upper surface of the body 112 of any one link 110 and the second rolling-contact portions 116a and 116b formed at the lower surface of the body 112 of another link 110 occurs, whereby a pan motion is realized.

As such, an extension length of any one of the first wires 181a and 181b is non-symmetric to a contraction length of the other one during implementation of a tilt motion of the arm unit 10, and an extension length of any one of the second wires 182a and 182b is non-symmetric to a contraction length of the other one during implementation of a pan motion of the arm unit 10. That is, tension applied to the first wires 181a and 181b and the second wires 182a and 182b is proportional to stiffness of the arm unit 10 made up of the plurality of links 100.

FIGS. 6A, 6B, 7A and 7B are views explaining a relationship between tension applied to the wires and stiffness of the arm unit.

Here, 'n' represents the number of links 110, '$\Phi_p$' and '$\Phi_t$' respectively represent angles between the respective neighboring links 110 during a pan motion and during a tilt motion, '$\Theta_p$' and '$\Theta_t$' respectively represent angles between the links 110 located at distal ends during a pan motion and during a tilt motion, '$L_{pl}$' and '$L_{pr}$' respectively represent lengths of portions of the second wires 182a and 182b connecting the respective neighboring links 110 to one another, and '$d_{pl}$' and '$d_{pr}$' respectively represent overall lengths of the second wires 182a and 182b.

Referring to FIGS. 6A and 6B, an extension length or contraction length of the second wires 182a and 182b is derived using a relationship between the above variables as follows:

$$\theta p = n \cdot \Phi p$$

$$\theta t = n \cdot \Phi t$$

$$L_{pl}(\phi_p, \phi_t) = 2r\left(1 - \cos\left(\alpha - \frac{\phi_p}{2}\right)\right) + 2r\left(1 - \cos\frac{\phi_t}{2}\right)$$

$$L_{pr}(\phi_p, \phi_t) = 2r\left(1 - \cos\left(\alpha + \frac{\phi_p}{2}\right)\right) + 2r\left(1 - \cos\frac{\phi_t}{2}\right)$$

$$nL_{pl}(\phi_p, \phi_t) = d_{pl}(\theta_p, \theta_t) = 2nr\left(\cos\alpha - \cos\left(\alpha - \frac{\theta_p}{2n}\right) + 1 - \cos\frac{\theta_t}{2n}\right)$$

$$nL_{pr}(\phi_p, \phi_t) = d_{pr}(\theta_p, \theta_t) = 2nr\left(\cos\alpha - \cos\left(\alpha + \frac{\theta_p}{2n}\right) + 1 - \cos\frac{\theta_t}{2n}\right)$$

In this case, the sum of $d_{pl}(\theta_p, \theta_t)$ and $d_{pr}(\theta_p, \theta_t)$ is not zero. That is, the absolute value of an extension length of any one second wire 182a is different from the absolute value of a contraction length of the other second wire 182b while the arm unit 10 performs a tilt motion or a pan motion. This equally applies to the first wires 181a and 181b.

As such, due to non-symmetry of the first wires 181a and 181b and of the second wires 182a and 182b while the arm unit 10 performs a tilt motion or a pan motion, stiffness of the arm unit 10 may be changed via adjustment of tension of the first wires 181a and 181b and the second wires 182a and 182b.

Referring to FIGS. 7A and 7B, a relationship between tension T applied to the first wires 181a and 181b and the second wires 182a and 182b and stiffness K of the arm unit 10 is derived as follows:

$$x = \frac{h}{\theta}(1 - \cos\theta)$$

$$d_{pl} = d_{pr} = d_p = nr\left(2\cos\alpha - \cos\left(\alpha - \frac{\theta}{n}\right) - \cos\left(\alpha + \frac{\theta}{n}\right)\right)$$

-continued $$d_{tl} = d_{tr} = d_t = 2nr\left(1 - \cos\frac{\theta}{n}\right)$$

Here, as illustrated in FIG. 7B, the following equations are acquired based on the concept of virtual work.

$$F\Delta x + T_p \Delta d_p + T_t \Delta d_t = 0$$

$$F = -T\frac{\Delta d_p + \Delta d_t}{\Delta_x}, T \equiv T_p = T_t$$

$$F = -T\left(\frac{\partial d_p}{\partial \theta} + \frac{\partial d_t}{\partial \theta}\right) \bigg/ \frac{\partial x}{\partial \theta}$$

$$\frac{\partial x}{\partial \theta} = -\frac{h}{\theta^2}(1 - \cos\theta) + \frac{h}{\theta}\sin\theta$$

$$\frac{\partial d_p}{\partial \theta} = r\left(\sin\left(\alpha + \frac{\theta}{n}\right) - \sin\left(\alpha - \frac{\theta}{n}\right)\right)$$

$$\frac{\partial d_t}{\partial \theta} = 2r\sin\frac{\theta}{n}$$

Arranging the above equations, $$K = \frac{F}{x} = -\frac{T}{h}\frac{\theta}{h(1-\cos\theta)}\left(\frac{\partial d_p}{\partial \theta} + \frac{\partial d_t}{\partial \theta}\right) \bigg/ \frac{\partial x}{\partial \theta}$$

$$K\big|_{\theta \to 0} = \frac{8r(\cos\alpha + 1)}{nh^2}T$$

As will be appreciated from the above equations, tension T applied to the first wires 181a and 181b and the second wires 182a and 182b and stiffness K of the arm unit 10 are proportional to one another, and thus stiffness K of the arm unit 10 may be changed by adjusting tension T of the first wires 181a and 181b and the second wires 182a and 182b.

With the above-described configuration, it may be possible to provide the arm unit 10 with flexibility by reducing stiffness while the arm unit 10 moves to a body part to be operated upon along curved internal organs of a patient, and to increase stiffness of the arm unit 10 so as to endure a load applied to the arm unit 10 while the arm unit 10 performs surgery after reaching the body part to be operated upon, which ensures more efficient implementation of surgery.

FIGS. 8A to 8C are views illustrating insertion of an anti-slip member through the links constituting the arm unit according to an embodiment.

As illustrated in FIGS. 8A to 8C, the anti-slip member 150 is located between the respective neighboring links 110 to prevent slippage that may occur during pivoting of the respective links 110.

The anti-slip member 150 has a combined shape of a part of the upper surface and a part of the lower surface of the body 112 of the respective links 110, so as to come into contact at one surface 150a and the other surface 150b thereof with the respective neighboring links 110. The anti-slip member 150 may be formed of a material that is different than the links' 110 material, and in particular may be formed of a plastic material or rubber material that is efficacious in anti-slip.

FIGS. 9A to 9C are views illustrating an arm unit according to another embodiment.

Except for toothed portions 214 and 216 of respective links 210 of an arm unit 20, other parts and a driving principle thereof are similar to the links 110 of the arm unit 10, and thus a description thereof is omitted.

As illustrated in FIGS. 9A to 9C, the respective links 210 of the arm unit 20 further may include toothed portions 214 and 216 to prevent slip during relative pivoting of the links 210.

The toothed portions 214 and 216 may include a first curvilinear toothed portion 214 and a second curvilinear toothed portion, which are respectively formed at an upper surface and a lower surface of a body 212 of the link 210.

The first toothed portion 214 and the second toothed portion 216 are formed in a circumferential direction of the upper surface and the lower surface of the body 212.

The first toothed portion 214 formed at any one of a plurality of links 210 is engaged with the second toothed portion 216 formed at another link 210 located thereabove, which prevents slippage that may occur while the respective neighboring links 110 come into rolling contact with one another to perform pivoting relative to one another.

FIGS. 10A to 10C are views illustrating an arm unit according to another embodiment.

As illustrated in FIGS. 10A to 10C, the arm unit 30 of the present embodiment may include, for example, a first link 310, a second link 320 and a third link 330. The second link 320 may be located neighboring an upper surface 312a of the first link 310 to come into rolling contact with the first link 310, and the third link 330 may be located neighboring an upper surface 322a of the second link 320 to come into surface contact with the second link 320.

Although the second link 320 and the third link 330 have been described above as being located neighboring the upper surface 312a of the first link 310 and the upper surface 322a of the second link 320 respectively, it will be clearly understood that the second link 320 and the third link 330 may be located respectively neighboring a lower surface 312b of the first link 310 and a lower surface 322b of the second link 320.

The first link 310 is similar to the above-described link 110 of the arm unit 10, and thus a detailed description thereof is omitted.

The third link 330 may include a centrally-hollowed body 332, and first flat portion 334a and 334b and second flat portions 336a and 336b formed respectively at an upper surface 332a and a lower surface 332b of the body 332 to come into surface contact with the neighboring second or third link 320 or 330.

The second link 320 is located between the first link 310 and the third link 330 to connect the first link 310 and the third link 330 to each other. The second link 320 includes a centrally-hollowed body 322, third flat portions 324a and 324b formed at a first surface 322a of the body 322, and third rolling-contact portions 326a and 326b formed at a second surface 322b opposite to the first surface 322a.

The third flat portions 324a and 324b are substantially equal to the first flat portions 334a and 334b or the second flat portions 336a and 336b formed at the third link 330. The third rolling-contact portions 326a and 326b are substantially equal to the first rolling-contact portions 314a and 314b or the second rolling-contact portions 316a and 316b formed at the first link 310.

In an embodiment, at least two first links 310 may be arranged neighboring each other to enable a tilt motion and a pan motion of the arm unit 30 via relative pivoting thereof, and at least two third links 330 may be arranged neighboring each other so as to serve as rigid bodies during a tilt motion and a pan motion of the arm unit 30. As illustrated in FIG. 10O, when tension is applied to wires 380a and 380b connecting the first, second and third links 310, 320 and 330 to one another, the third links 330 serve as rigid bodies to maintain stiffness of the arm unit 30, and the first links 310 may pivot relative to one another to enable a tilt motion and a pan motion of the arm unit 30.

FIGS. 11A, 11B and 11C are views illustrating an arm unit according to a further embodiment.

As illustrated in FIGS. 11A to 11C, the arm unit 40 may include a first link 410 having symmetric upper and lower portions and a second link 420 having asymmetric upper and lower portions.

The first link 410 is similar to the above-described link 110 of the arm unit 10, and thus a detailed description thereof is omitted.

The second link 420 includes a centrally-hollowed body 422, fourth rolling-contact portions 424a and 424b formed at a first surface 422a of the body 422, and fifth rolling-contact portions 426a and 426b formed at a second surface 422b opposite to the first surface 422a.

The body 422 is asymmetrically configured such that one side extends more than the other side in a pivoting direction of the first link 410 or the second link 420 during a tilt motion or a pan motion of the arm unit 40, which causes a height difference between the fourth rolling-contact portions 424a and 424b.

The first link 410 and the second link 420 are alternately arranged at 90°-rotated positions relative to each other, causing the arm unit 40 to be initially tilted as during implementation of a tilt motion or a pan motion. This allows the arm unit 40 to perform a tilt motion or a pan motion at a greater angle, and consequently increases a reachable range of the arm unit 40 to a body part to be operated upon, etc.

As is apparent from the above description, an arm unit made up of a plurality of links according to the embodiments is adjustable in stiffness via tension adjustment of wires.

Although the embodiments of the present disclosure have been shown and described, it would be appreciated by those skilled in the art that changes may be made in these embodiments without departing from the principles and spirit of the disclosure, the scope of which is defined in the claims and their equivalents.

What is claimed is:

1. An apparatus comprising:
an arm unit including,
a plurality of links coming into rolling contact with one another via a plurality of regions of each of the links, each of the plurality of links includes a plurality of first rolling contact portions convexly curved towards a first neighbor link of the plurality of links and a plurality of second rolling contact portions concavely curved towards a second neighbor link of the plurality of links such that each of the plurality of first rolling contact portions make point contact at respective ones of two points with the plurality of second rolling contact portions of the first neighbor link and each of the plurality of second rolling contact portions make point contact at a respective ones of two points with the plurality of second rolling contact portions of the second neighbor link, and
a plurality of wires penetrating each of the plurality of links to connect the links to one another, whereby the connected links articulate the arm unit, the plurality of wires including a pair of first wires arranged at respective ones of a first set of two opposing maximum points of the plurality of first rolling contact portions that are convex and a pair of second wires arranged at respective ones of a second set of two opposing minimum points associated with the plurality of second rolling contact portions that are concave; and
a drive unit, the drive unit including a pair of drive plates, the pair of drive plates pivotally connected to the drive unit, the pair of drive plates each including a semicircular lower portion having a respective one of the pair of first wires and the pair of second wires strung around a circumference thereof such that the pair of drive plates are configured to adjust tension applied to the respective one of the pair of first wires and the pair of second wires when a drive motor pivots a respective one of the pair of drive plates, wherein
an extension length of a first one of the pair of first wires is non-symmetric with respect to a contraction length of a second one of the pair of first wires during driving of the arm unit, the arm unit performing a tilt motion in response to a tension being applied to the first pair of wires, and performing a pan motion in response to a tension being applied to the second pair of wires such that a stiffness of the arm unit is adjustable by varying the tension of one or more of the first one of the pair of first wires and the second one of the pair of first wires during the tilt motion or the pan motion of the arm unit.

2. The apparatus according to claim 1, wherein the plurality of links is arranged in series, and at least two links among the plurality of links come into rolling contact with neighboring links.

3. The apparatus according to claim 2, wherein at least one link among the plurality of links includes a centrally-hollowed body.

4. The apparatus according to claim 3, wherein the plurality of first rolling contact portions include a pair of first rolling-contact portions arranged at 180° rotated positions from each other with respect to a center axis of the body and in a longitudinal direction of the body.

5. The apparatus according to claim 4, wherein the plurality of second rolling contact portions include a pair of second rolling-contact portions arranged at 180° rotated positions from each other with respect to the center axis of the body in the longitudinal direction of the body.

6. The apparatus according to claim 5, wherein the first rolling-contact portions and the second rolling-contact portions are arranged at 90 degree rotated positions from each other with respect to the center axis of the body and in a circumferential direction of the body.

7. The apparatus according to claim 5, wherein
the pair of first wires penetrate the first rolling contact portions in an arrangement direction of the plurality of links; and the pair of second wires penetrate the second rolling contact portions in an arrangement direction of the plurality of links.

8. The apparatus according to claim 3, wherein a part of the first rolling contact portion is a part of a circle having a predetermined curvature.

9. The apparatus according to claim 3, wherein the plurality of links includes:
a first link; and
a second link to come into rolling contact with an upper surface or a lower surface of the first link at a 90° rotated position with respect to the first link on the basis of a center axis penetrating the center of the first link in a longitudinal direction of the body.

10. The apparatus according to claim 9, further comprising an anti-slip member located between the first link and the second link to prevent slip between the first link and the second link.

11. The apparatus according to claim 10, wherein one surface of the anti-slip member comes into contact with a part of the first link, and another surface comes into contact with a part of the second link.

12. The apparatus according to claim 9, wherein a first surface of the first link a second surface of the second link are each respectively provided with a first toothed portion and a second toothed portion, which are engaged with each other to prevent slip between the first link and the second link.

13. The apparatus according to claim 12, wherein the first toothed portion is circumferentially formed at the first surface of the first link, which has a centrally-hollowed shape, and the second toothed portion is circumferentially formed at the second surface of the second link, which has a centrally-hollowed shape.

14. The apparatus according to claim 3, wherein the first rolling contact portions have different heights.

15. The apparatus according to claim 2, wherein the plurality of links includes:
a first link having upper and lower surfaces, each of which comes into rolling contact with other neighboring links;
a second link having upper and lower surfaces, one of which comes into rolling contact with another neighboring link, and the other one of which comes into surface contact with another neighboring link; and
at least one third link having upper and lower surfaces, each of which comes into surface contact with other neighboring links.

16. The apparatus according to claim 15, wherein the second link is located in between the first link and the third link.

17. The apparatus according to claim 16, wherein the at least one third link includes at least two third links arranged neighboring each other to serve as rigid bodies during driving of the arm unit.

18. An apparatus comprising:
an arm unit having a plurality of links and a plurality of wires penetrating the links to couple the links to one another, each of the plurality of links includes (i) a centrally-hollowed body, (ii) a plurality of first rolling contact portions convexly curved towards a first neighbor link of the plurality of links and (iii) a plurality of second rolling contact portions concavely curved towards a second neighbor link of the plurality of links such that each of the plurality of first rolling contact portions make point contact at respective ones of two points with the plurality of second rolling contact portions of the first neighbor link and each of the plurality of second rolling contact portions make point contact at a respective ones of two points with the plurality of second rolling contact portions of the second neighbor link, the plurality of wires including a pair of first wires arranged at respective ones of a first set of two opposing maximum points of the plurality of first rolling contact portions that are convex portions and a pair of second wires arranged at respective ones of a second set of two opposing minimum points of the plurality of second rolling contact portions that are concave portions, the arm unit performing a tilt motion in response to a tension being applied to the first pair of wires, and performing a pan motion in response to a tension being applied to the second pair of wires such that a stiffness of the arm unit is adjustable by varying the tension of one or more wires included in the pair of first wires and the pair of second wires during the tilt motion or the pan motion of the arm unit; and
a drive unit to drive the arm unit via the plurality of wires, the drive unit including a pair of drive plates, the pair of drive plates pivotally connected to the drive unit, the pair of drive plates each including a semicircular lower portion having a respective one of the pair of first wires and the pair of second wires strung around a circumference thereof such that the pair of drive plates are configured to adjust tension applied to the respective one of the pair of first wires and the pair of second wires when a drive motor pivots a respective one of the pair of drive plates.

19. The apparatus according to claim 18, wherein each of the links include at least one concave portion connected to the convex portion, and
wherein the concave portion associated with a respective one of the links defines a pivoting space to allow the respective link and another link neighboring the respective link to pivot relative to each other via the convex portions thereof.

20. The apparatus according to claim 19, wherein the at least one convex portion includes a pair of convex portions arranged opposite to each other on the basis of an imaginary first division plane including a center axis of the body.

21. The apparatus according to claim 20, wherein the at least one concave portion includes a pair of concave portions arranged opposite to each other on the basis of an imaginary second division plane perpendicular to the first division plane.

22. The apparatus according to claim 20, wherein each of the pair of convex portions is raised by different lengths.

23. The apparatus according to claim 18, wherein the plurality of links includes a first link, and second and third links both having the same shape as the first link and arranged respectively neighboring an upper surface and a lower surface of the first link,
wherein the first link includes a centrally-hollowed body, a pair of first convex portions longitudinally raised from a part of an upper surface of the body to come into rolling contact with the second link, and a pair of second convex portions raised from a part of a lower surface of the body in a direction opposite to the raised direction of the first convex portions to come into rolling contact with the third link, and
wherein the second convex portions are located at 90° rotated positions with respect to the first convex portions on the basis of a center axis of the body in a longitudinal direction of the body.

24. The apparatus according to claim 23, wherein the second link includes a centrally-hollowed body, a pair of third convex portions longitudinally raised from a part of an upper surface of the body to come into rolling contact with another link neighboring an upper surface of the second link, and a pair of fourth convex portions raised from a part of a lower surface of the body in a direction opposite to the raised direction of the first convex portions to come into rolling contact with the first link, and wherein the pair of fourth convex portions respectively comes into rolling contact with the pair of first convex portions.

25. The apparatus according to claim 24, further comprising an anti-slip member located between the first link and the second link to prevent slip between the first link and the second link, wherein one surface of the anti-slip member comes into contact with the first convex portions, and the other surface comes into contact with the fourth convex portions.

26. The apparatus according to claim 24, wherein the first convex portions and the fourth convex portions each comprise toothed portions to allow at least a part of the first convex portions and at least a part of the fourth convex portions to engage with each other, to prevent slip between the first link and the second link.

27. A robot arm comprising:

a plurality of links sequentially coupled to one another in a rolling-contact manner, each of the links including a plurality of first rolling contact portions convexly curved towards a first neighbor link of the plurality of links and a plurality of second rolling contact portions concavely curved towards a second neighbor link of the plurality of links such that each of the plurality of first rolling contact portions make point contact at respective ones of two points with the plurality of second rolling contact portions of the first neighbor link and each of the plurality of second rolling contact portions make point contact at a respective ones of two points with the plurality of second rolling contact portions of the second neighbor link;

a plurality of wires penetrating the links to couple the links to one another, the plurality of wires including a pair of first wires arranged at respective ones of a first set of two opposing maximum points of the plurality of first rolling contact portions that are convex portions and a pair of second wires arranged at respective ones of a second set of two opposing minimum points of the plurality of first rolling contact portions that are concave portions, the robot arm performing a tilt motion in response to a tension being applied to the first pair of wires, and to perform a pan motion in response to a tension being applied to the second pair of wires such that a stiffness of the robot arm is adjustable by varying the tension of one or more wires included in the pair of first wires and the pair of second wires during the tilt motion or the pan motion of the robot arm; and a drive unit, the drive unit including a pair of drive plates, the pair of drive plates pivotally connected to the drive unit, the pair of drive plates each including a semicircular lower portion having a respective one of the first pair of wires and the second pair of wires strung around a circumference thereof such that the pair of drive plates are configured to adjust tension applied to the respective one of the first pair of wires and the second pair of wires when a drive motor pivots a respective one of the pair of drive plates.

28. A robot arm comprising:

a plurality of links sequentially coupled with each other in a rolling contact manner, the plurality of links including a first link, a second link and a third link sequentially arranged, the second link including a centrally-hollowed body, a plurality of first rolling contact portions convexly curved towards the first link and a plurality of second rolling contact portions concavely curved towards the third link such that each of the plurality of first rolling contact portions make point contact at respective ones of two points with the plurality of second rolling contact portions of the first link and each of the plurality of second rolling contact portions make point contact at a respective ones of two points with the plurality of second rolling contact portions of the third link;

a plurality of wires penetrating the links to connect the links to one another such that (i) a first wire of the plurality of wires penetrates a hole disposed at a maximum point in one of the plurality of first rolling contact portions of the first link and penetrates a hole disposed at a minimum point in one of the plurality of second rolling contact portions of the second link thereby connecting the first link and the second link to form an articulated portion of the robot arm, and (i) a second wire of the plurality of wires penetrates a hole disposed at a minimum point in one of the plurality of first rolling contact portions of the first link and penetrates a hole disposed at a maximum point in one of the plurality of second rolling contact portions of the second link thereby further connecting the first link and the second link; and a drive unit, the drive unit including a pair of drive plates, the pair of drive plates pivotally connected to the drive unit, the pair of drive plates each including a semicircular lower portion having a respective one of the first wires and the second wires strung around a circumference thereof such that the pair of drive plates are configured to adjust tension applied to the respective one of the first wires and the second wires when a drive motor pivots a respective one of the pair of drive plates, wherein the robot arm performs a tilt motion in response to a tension being applied to the first wire, and performs a pan motion in response to a tension being applied to the second wire such that a stiffness of the robot arm is adjustable by varying the tension of one or of the first wire and the second wire during the tilt motion or the pan motion of the robot arm.

\* \* \* \* \*